US006869944B2

(12) United States Patent
Pamukcu et al.

(10) Patent No.: US 6,869,944 B2
(45) Date of Patent: *Mar. 22, 2005

(54) METHOD FOR TREATING A PATIENT WITH NEOPLASIA BY TREATMENT WITH A PLATINUM COORDINATION COMPLEX

(75) Inventors: Rifat Pamukcu, Spring House, PA (US); Kerstin B. Menander, Meadowbrook, PA (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/228,700

(22) Filed: Aug. 27, 2002

(65) Prior Publication Data

US 2003/0113382 A1 Jun. 19, 2003

Related U.S. Application Data

(63) Continuation of application No. 10/039,154, filed on Jan. 3, 2002, now abandoned, which is a division of application No. 09/777,395, filed on Feb. 6, 2001, now Pat. No. 6,359,002, which is a continuation of application No. 09/190,830, filed on Nov. 12, 1998, now Pat. No. 6,235,782.

(51) Int. Cl.$^7$ ..................... A61K 31/555; A61K 31/519
(52) U.S. Cl. .................... 514/184; 514/261.1; 514/570; 514/673
(58) Field of Search ................................. 514/184, 673, 514/570, 261.1, 186; 544/64, 225; 540/201; 548/402; 546/5, 11; 549/206

(56) References Cited

U.S. PATENT DOCUMENTS 6,235,782 B1 * 5/2001 Pamukcu et al. ........... 514/532

OTHER PUBLICATIONS

Eichholtz–Wirth, H., "Reversal of radiation–induced cisplatin resistance in murine fibrosarcoma cells by selective modulation of the cyclic GMP–dependent transduction pathway.", abstract of British Journal of Cancer, 72(2), pp 287–292, Aug. 1995.*

* cited by examiner

*Primary Examiner*—Dwayne Jones
(74) *Attorney, Agent, or Firm*—Shu Lee

(57) ABSTRACT

This invention provides a method for treating a patient with neoplasia by an adjuvant therapy that includes treatment with an antineoplastic platinum coordination complex.

3 Claims, 15 Drawing Sheets

METHOD FOR TREATING A PATIENT WITH NEOPLASIA BY TREATMENT WITH A PLATINUM COORDINATION COMPLEX

This application is a Continuation of prior U.S. application Ser. No. 10/039,154 filed Jan. 3, 2002, which is now abandoned, entitled "Method for Treating a Patient with Neoplasia by Treatment with a Platinum Coordination Complex," which is a Divisional of prior U.S. application Ser. No. 09/777,395 filed Feb. 6, 2001, which is now U.S. Pat. No. 6,359,002, entitled "Method for Treating a Patient with Neoplasia by Treatment with a Platinum Coordination Complex," which is a Continuation of prior U.S. application Ser. No. 09/190,830 filed Nov. 12, 1998, which is now U.S. Pat. No. 6,235,782, entitled "Method for Treating a Patient with Neoplasia by Treatment with a Platinum Coordination Complex," all of which are incorporated herein by reference.

BACKGROUND OF THE INVENTION

Virtually all of the many antineoplastic drugs that are currently used in the treatment of cancer have very serious and harmful side effects. This is because cancer is generally treated with medications that interfere with the growth of rapidly dividing cells. Such medications can inhibit the growth of the cancer cells, but they almost always also inhibit the growth of normal cells that divide rapidly in the body. Some of the normal tissues that divide very rapidly include bone marrow (which produces blood cells), hair follicles, and intestinal epithelium. The usefulness of virtually all antineoplastic drugs is severely limited by the damage they cause to these normal tissues.

This invention relates to methods for treating neoplasia using both an antineoplastic platinum coordination complex (a common chemotherapeutic) and a cyclic GMP (cGMP)-specific phosphodiesterase (PDE) inhibitor to reduce the side effects or increase the efficacy of treatment with an antineoplastic platinum coordination complex. Under current practices, platinum complexes (e.g., cisplatin and carboplatin) are typically used to treat certain cancers, particularly ovarian and testicular cancers.

Cisplatin (cis-diaminedichloroplatinum) is a heavy metal complex with a central platinum atom surrounded by two ammonia molecules and two chlorine atoms in the cis position. Cisplatin is also known by the trade name Platinol.

Cisplatin is typically used as a secondary therapy in combination with other chemotherapeutic agents for metastatic testicular tumors and metastatic ovarian tumors in patients who have already received appropriate surgical or radiotherapeutic treatment. Cisplatin is also used as a single agent in treating patients with transitional cell bladder cancer which is not suited for surgical or radiotherapeutic treatment. Cisplatin has been used in treating epithelial malignancies as well as cancers of the head and neck, the esophagus, and the lung Cisplatin appears to enter cells by diffusion. The chlorine atoms of cisplatin are subject to chemical displacement by nucleophiles, such as water or sulthydryl groups. The activated species of the drug reacts with nucleic acids and proteins. Platinum complexes can react with DNA, forming both intrastrand and interstrand crosslinks, which inhibit DNA replication and RNA transcription and can lead to breaks and miscoding. The platinum from cisplatin also becomes bound to several plasma proteins including albumin, transferring, and gamma globulin which may interfere with a number of cellular functions.

The major dose-limiting toxicity of cisplatin is cumulative renal insufficiency which has been associated with renal tubular damage. Renal toxicity becomes more prolonged and more severe with repeated cisplatin treatments. Electrolyte disturbances are often secondary effects of renal damage. Hydration and diuresis are used to reduce renal toxicity, but renal damage often occurs even if these measures are taken.

Myelosuppression is another dose-related toxicity of cisplatin treatment, characterized by a decrease in the levels of leukocytes and platelets. Leukocytes are white blood cells which fight off infection, and platelets are necessary for proper blood clotting. Anemia is another side effect of treatment with cisplatin.

Toxic reactions in the ears, or otoxicity is another effect of cisplatin treatment. This can be manifested by tinnitus, or noises such as ringing or whistling in the ears, loss of high frequency hearing, and occasionally deafness. It is unclear whether cisplatin-related ototoxicity is reversible.

Other side effects of cisplatin include gastrointestinal effects such as nausea and vomiting which occur in almost all patients treated with cisplatin. Anaphylactic-like reactions may occur shortly after administration of the drug.

Cisplatin is a member of the family of platinum coordination complexes. There are numerous derivatives of cis-platinum including carboplatin and oxaliplatin. Carboplatin (Paraplatin), like cisplatin, is thought to produce interstrand DNA cross-links. It is currently used in the treatment of patients with ovarian cancer that has recurred after chemotherapy. Clinically, there is less nephrotoxicity with carboplatin than with cisplatin, and the dose-limiting toxicity with carboplatin is myelosupression, primarily as thrombocytopenia, or a decrease in the platelets in the blood.

SUMMARY OF THE INVENTION

This invention relates to an improved method of cancer therapy that involves treating a patient with both an antineoplastic platinum coordination complex (i.e., a cisplatin derivative, which includes both cisplatin and derivatives thereof such as carboplatin) and a cGMP-specific phosphodiesterase (PDE) inhibitor. The specific PDE inhibitors useful for this invention are compounds that inhibit both PDE5 and the new cGMP-specific PDE described below. The novel cGMP-PDE is fully described by Liu. et al., in the copending U.S. patent application Ser. No. 09/173,375 (Case No. P-143), A Novel Cyclic GMP-Specific Phosphodiesterase And Methods For Using Same In Pharmaceutical Screening For Identifying Compounds For Inhibition Of Neoplastic Lesions. (For general PDE background, see. Beavo, J. A. (1995) Cyclic nucleotide phosphodiesterases: functional implications of multiple isoforms. Physiological Reviews 75:725–747; web site <http://weber.u.washington.edu/~pde/pde.html> (November 1998)).

In this invention, the cGMP-specific PDE inhibitor can be used in combination with an antineoplastic platinum coordination complex in two ways. The first is a lower dosage methodology in which the traditionally recommended dose range of the cisplatin derivative is decreased while its therapeutic effects are maintained and its side effects are attenuated. The second is a higher dosage methodology that utilizes the traditionally recommended dose range for the cisplatin derivative and improves its activity without increasing its side effects. With each methodology, the cisplatin derivative is administered simultaneously with or in succession with an appropriate cGMP-specific PDE inhibitor.

In the low dose regime, a cisplatin derivative is administered at doses less than about 75 mg m$^2$. In the high dose regime, a cisplatin derivative is administered at doses between about 75 and 100 mg/m$^2$.

DETAILED DESCRIPTION OF THE PREFERRED EMBODIMENTS

Figure 1:
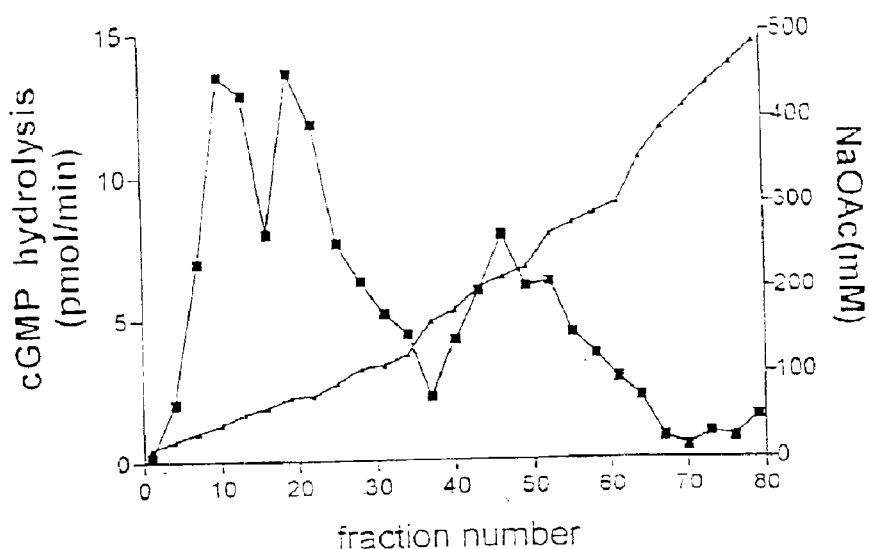
FIG. 1 is a graph of the cGMP activities of the cGMP phosphodiesterases obtained from SW-480 neoplastic cells, as assayed from a the eluent from a DEAE-Trisacryl M column.

As discussed in greater detail below, the inhibition of cGMP-specific PDEs can induce apoptosis in neoplastic cells. Cisplatin derivatives are currently used to treat neoplasias, particularly ovarian and testicular cancers. The combination of these two types of therapies can produce an effect that neither can produce individually.

I. The Novel cGMP-Specific Phosphodiesterase

A new cyclic GMP-specific phosphodiesterase has been discovered in neoplastic cells. Treatment of cells with a compound that inhibits both PDE5 and this novel cGMP-specific PDE leads to apoptosis of the neoplastic cells. In other words, the preferred cGMP-specific inhibitors useful in this invention, in combination with a cisplatin derivative are those compounds that inhibit both PDE5 and this new PDE.

The new PDE is broadly characterized by
(a) cGMP specificity over cAMP;
(b) positive cooperative kinetic behavior in the presence of cGMP substrate;
(c) submicromolar affinity for cGMP; and
(d) insensitivity to incubation with purified cGMP-dependent protein kinase.

As discussed below, this new cGMP-PDE is unique from the classical PDE5. Kinetic data reveal that the new PDE has increased cGMP hydrolytic activity in the presence of increasing cGMP substrate concentrations, unlike PDE5 which exhibits cGMP substrate saturation. The new cGMP-PDE is insensitive to incubation with cGMP-dependent protein kinase (PKG), whereas PDE5 is phosphorylated by PKG. Additionally, the new cGMP-PDE is relatively insensitive to inhibition with PDE5-specific inhibitors, zaprinast and E4021. Finally, the new cGMP-PDE activity can be separated from classical PDE5 activity by anion-exchange chromatography.

The new cGMP-PDE is not a member of any of the other previously characterized PDE families. The new PDE does not hydrolyze cAMP significantly. Calcium (with or without calmodulin) failed to activate either cAMP or cGMP hydrolysis activity, indicating that the novel PDE is not a CaM-PDE (PDE1). Additionally, cGMP failed to activate or inhibit cAMP hydrolysis, indicating that the new cGMP-PDE it is not a cGMP-stimulated PDE (cGS-PDE or PDE2), because all known isoforms of the PDE2 family hydrolyze both cAMP and cGMP. Further, the new cGMP-PDE is insensitive to a number of specific PDE inhibitors. It is relatively insensitive to vinpocetine (a CaM-PDE- or PDE1-specific inhibitor), to indolodan (a cG1-PDE- or PDE3-specific inhibitor), and to relipram (a cAMP-PDE- or PDE4-specific inhibitor). The data establish that the new PDE is not a member of one of the cAMP-hydrolyzing PDE families (PDE1, PDE2, PDE3, or PDE4).

PDE inhibitors that are useful for treating patients with neoplasia-consistent with this invention should inhibit both PDE5 and the new cGMP-PDE. A compound that inhibits both forms of cGMP-specific PDE is desirable because a compound that inhibits PDE5 but not the new PDE, does not by itself induce apoptosis. For example, zaprinast, sildenafil, and E4021 have been reported as potent inhibitors of PDE5. However, compared to PDE5, the new PDE is relatively insensitive to zaprinast, sildenafil, and E4021 (Table 1). And none of the three, zaprinast, sildenafil, or E4021, have been found to induce apoptosis (Table 6) or to inhibit cell growth in neoplastic cells (Tables 3 and 4).

However, a number of PDE5 inhibitors have been found to induce apoptosis in neoplastic cells. Examples of such compounds are sulindac sulfide and Compound E. Sulindac sulfide and Compound E each inhibit PDE5 and the new cGMP-PDE with the same potency (Table 1). And both sulindac sulfide and Compound E induce apoptosis in neoplastic cells (Table 6). Compounds that inhibit PDE5, but not the new cGMP-PDE, do not cause apoptosis in neoplastic cells. But compounds that inhibit both PDE5 and the new cGMP-PDE, have been found to induce apoptosis in neoplastic cells.

A. Isolation of the Novel cGMP-Specific Phosphodiesterase

The novel cGMP-specific phosphodiesterase can be isolated from human carcinoma cell lines (e.g. SW-480, a human colon cancer cell line that originated form a moderately differentiated epithelial adenocarcinoma, available from the American Tissue Type Collection in Rockville, Md., U.S.A.). The complete isolation of this new cGMP-PDE is described in U.S. Pat. No. 6,200,771, which is incorporated herein by reference.

Briefly, to isolate the novel phosphodiesterase, SW-480 cells are collected and homogenized. The homogenate is centrifuged, and the supernatant is loaded onto a DEAE-Trisacryl M column. The loaded column is then washed, and PDE activities are eluted with a linear gradient of NaOAc. Fractions are collected and immediately assayed for cGMP hydrolysis activity. Cyclic nucleotide PDE activity of each fraction is determined using the modified two-step radioisotopic method of Thompson et al. (Thompson W. J., et al., Adv Cyclic Nucleotide Res 10: 69–92, 1979). There are two initial peaks of cGMP-PDE activity eluted from the column, peak A and peak B (see FIG. 1). Peak A is PDE5, whereas peak B is the new cGMP-PDE.

Figure 2:
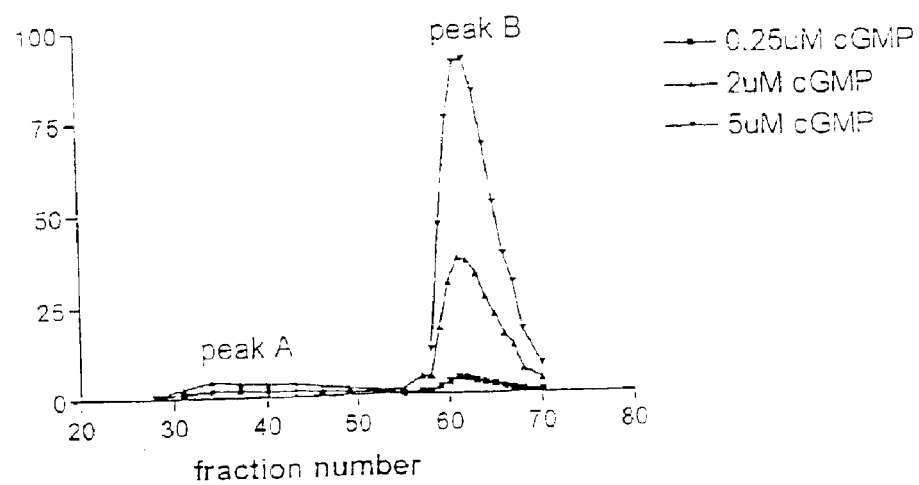
FIG. 2 is a graph of cGMP activities of the reloaded cGMP phosphodiesterases obtained from SW-480 neoplastic cells, as assayed from a the eluent from a DEAE-Trisacryl M column.

To further fractionate the cGMP hydrolytic activity of PDE5 and the new cGMP-PDE, the fractions containing those activities are reloaded onto the DEAE-Trisacryl M column and eluted with a linear gradient of $N_2OAc$. Fractions are again immediately assayed for cGMP hydrolysis activity, the results of which are presented in FIG. 2. As illustrated in FIG. 2, peak B, the novel PDE, shows enhanced activity with increasing cGMP substrate concentration. Peak A, on the other hand, shows apparent substrate saturation with increasing concentrations of cGMP.

cGMP-Specificity of PDE Peaks A and B

Each fraction from the DEAE column was also assayed for cGMP-hydrolysis activity (0.25 $\mu$M cGMP) in the presence or absence of $Ca^-$, or $Ca^-$-CaM and/or EGTA and for cAMP (0.25 $\mu$M cAMP) hydrolysis activity in the presence or absence of 5 $\mu$M cGMP. Neither PDE peak A nor peak B (fractions 5–22; see FIG. 1) hydrolyzed cAMP significantly, establishing that neither was a member of a cAMP hydrolyzing family of PDEs (i.e. a PDE 1, 2, 3).

$Ca^-$ (with or without calmodulin) failed to activate either cAMP or cGMP hydrolysis activity of either peak A or B, and cGMP failed to activate or inhibit cAMP hydrolysis. Such results establish that peaks A and B constitute cGMP-specific PDEs but not PDE1, PDE2, PDE3, or PDE4.

For PDE peak B, as discussed below, cyclic GMP activated the cGMP hydrolytic activity of the enzyme, but did not activate any cAMP hydrolytic activity. This reveals that PDE peak B—the novel phosphodiesterase—is not a cGMP-stimulated cyclic nucleotide PDE ("cGS") or among the PDE2 family isoforms because the known isoforms of PDE2 hydrolyze both cGMP and cAMP.

C. Peak A is a PDE5, but Peak B—A New cGMP-Specific PDE—is not

To characterize any PDE isoform, kinetic behavior and substrate preference should be assessed. Peak A showed typical "PDE5" characteristics. For example, the $K_m$ of the enzyme for cGMP was 1.07 $\mu$M, and Vmax was 0.16 nmol/min/mg. In addition, as discussed below, zaprinast ($IC_{50}$=1.37 $\mu$M), E4021 ($IC_{50}$=3 nM), and sildenafil inhibited activity of peak A. Further, zaprinast showed inhibition for cGMP hydrolysis activity of peak A, consistent with results reported in the literature for PDE5.

Figure 3:
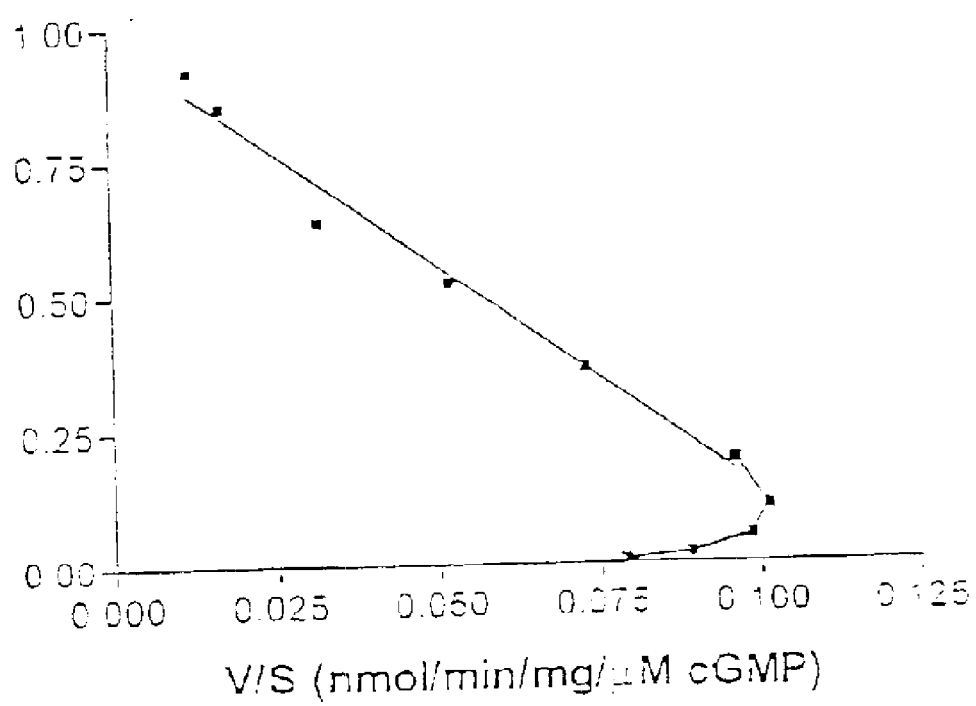
FIG. 3 is a graph of the kinetic behavior of the novel PDE.

PDE peak B showed considerably different kinetic properties as compared to PDE peak A. For example, in Eadie-Hofstee plots of peak A, cyclic GMP hydrolysis shows a single line with negative slope with increasing substrate concentrations, indicative of Michaelis-Menten kinetic behavior. Peak B, however, shows the novel property for cGMP hydrolysis in the absence of cAMP of a decreasing (apparent $K_m$=8.4), then increasing slope ($K_m$<1) of Eadie-Hofstee plots with increasing cGMP substrate (see FIG. 3). This establishes peak B's submicromolar affinity for cGMP (i.e. where $K_m$<1)

Consistent with the kinetic studies (i.e., FIG. 3) and positive-cooperative kinetic behavior in the presence of cGMP substrate, was the increased cGMP hydrolytic activity in the presence of increasing concentrations of cGMP substrate. This was discovered by comparing 0.25 $\mu$M, 2 $\mu$M, and 5 $\mu$M concentrations of cGMP in the presence of PDE peak B after a second DEAE separation to rule out cAMP hydrolysis and to rule out this new enzyme being a "classic" PDE5. Higher cGMP concentrations evoked disproportionately greater cGMP hydrolysis with PDE peak B, as shown in FIG. 2.

These observations suggest that cGMP binding to the peak B enzyme causes a conformational change in the enzyme.

D. Zaprinast- and Sildenafil-Insensitivity of PDE Peak B Relative to Peak A, and their Effects on Other PDE Inhibitors Different PDE inhibitors were studies using twelve concentrations of drug from 0.01 to 100 $\mu$M and substrate concentration of 0.25 $\mu$M $^3$H-cGMP, $IC_{50}$ values were calculated with variable slope, sigmoidal curve fits using Prism 2.01 (GraphPad). The results are shown in Table 1. While compounds E4021 and zaprinast inhibited peak A. (with high affinities) $IC_{50}$ values calculated against peak B are significantly increased (>50 fold). This confirms that peak A is a PDE5. These data further illustrate that the novel PDE is, for all practical purposes, zaprinast-insensitive and E4021-insensitive.

TABLE 1

Comparison of PDE Inhibitors Against Peak A and Peak B (cGMP Hydrolysis)

| Compound | PDE Family Inhibitor | $IC_{50}$ Peak A ($\mu$M) | $IC_{50}$ Peak B ($\mu$M) | Ratio ($IC_{50}$ Peak A Peak B) |
|---|---|---|---|---|
| E4021 | 5 | 0.003 | 8.4 | 0.0004 |
| Zaprinast | 5 | 1.4 | >30 | >0.05 |
| Compound E | 5 and others | 0.38 | 0.37 | 1.0 |
| Sulindac sulfide | 5 and others | 50 | 50 | 1.0 |
| Vinpocetine | 1 | >100 | >100 | |
| EHNA | 2.5 | >100 | 3.7 | |
| Indolidan | 3 | 31 | >100 | <0.31 |
| Rolipram | 4 | >100 | >100 | |
| Sildenafil | 5 | .0003 | >10 | <.00003 |

By contrast, sulindac sulfide and Compound E competitively inhibit both peak A and peak B phosphodiesterases at the same potency (for Compound E, $IC_{50}$=0.38 $\mu$M for PDE peak A; $IC_{50}$=0.37 $\mu$M for PDE peak B).

There is significance for the treatment of neoplasia and the selection of useful compounds for such treatment in the fact that peak B is zaprinast-insensitive whereas peaks A and B are both sensitive to sulindac sulfide and Compound E. Zaprinast, E4021, and sildenafil have been tested to ascertain whether they induce apoptosis or inhibit the growth of neoplastic cells, and the same has been done for Compound E. As explained below, zaprinast, sildenafil and E4021 do not have significant apoptosis-inducing (Table 6) or growth-inhibiting (Tables 3 and 4) properties, whereas sulindac sulfide and Compound E are precisely the opposite. In other words, the ability of a compound to inhibit both PDE peaks A and B correlates with its ability to induce apoptosis in neoplastic cells, whereas if a compound (e.g., zaprinast) has specificity for PDE peak A only, that compound will not induce apoptosis.

E. Insensitivity of PDE Peak B to Incubation with cGMP-Dependent Protein Kinase

Further differences between PDE peaks A and B were observed in their respective cGMP-hydrolytic activities in the presence of varying concentrations of cGMP-dependent protein kinase (PKG, which phosphorylates typical PDE5). Specifically, peak A and peak B fractions were incubated with different concentrations of protein kinase G at 30° C. for 30 minutes. Cyclic GMP hydrolysis of both peaks was assayed after phosphorylation was attempted. Consistent with previously published information about PDE5, peak A showed increasing cGMP hydrolysis activity in response to protein kinase G incubation, indicating that peak A was phosphorylated. Peak B was unchanged, however (i.e., was not phosphorylated and was insensitive to incubation with cGMP-dependent protein kinase). These data are consistent with peak A being a PDE5 family isoform and peak B being a novel cGMP-PDE.

II. Selecting a cGMP-Specific Phosphodiesterase Inhibitor for Use in this Invention Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth is affected by a test compound is important to the discovery of a relevant target for pharmaceutical therapy. Assays based on this technology can be combined with other tests to determine which compounds have growth inhibiting and pro-apoptotic activity.

In this invention particular cGMP-specific PDE inhibitors are selected for use in combination with a cisplatin derivative to treat neoplasia, especially ovarian and testicular cancers, in one of several ways. As indicated above, preferred PDE inhibitors are those that inhibit the activities of both PDE5 and the new cGMP-PDE. A compound can be selected for use in this invention by evaluating its effect on the cGMP hydrolytic activity on a mixture of the two enzymes (i.e., a mixture of peaks A and B) isolated from a tumor cell line. Alternatively, a compound can be selected by evaluating the compound's effect on cyclic nucleotide levels in whole neoplastic cells before and after exposure of the cells to the compound of interest. Still another alternative is to test a compound of interest against the two PDEs separately, i.e., by physically separating each activity from a tumor cell line (or by using recombinant versions of each enzyme) and testing the inhibitory action of the compound against each enzyme individually. With any of the above approaches, an appropriate PDE inhibitor can be selected for use in combination with a cisplatin derivative.

A. Phosphodiesterase Enzyme Assay

Phosphodiesterase activity (whether in a mixture or separately) can be determined using methods known in the art, such as a method using a radioactively labeled form of cGMP as a substrate for the hydrolysis reaction. Cyclic GMP labeled with tritium ($^3$H-cGMP) is used as the substrate for the PDE enzymes. (Thompson, W. J., Teraski, W. L., Epstein, P. M., Strada, S. J., *Advances in Cyclic Nucleotide Research*, 10:69–92, 1979, which is incorporated herein by reference). In this assay, cGMP-PDE activity is determined by quantifying the amount of cGMP substrate that is hydrolyzed either in the presence or absence of the test compound).

In brief, a solution of defined substrate $^3$H-cGMP specific activity is mixed with the drug to be tested. The mixture is incubated with isolated PDE activity (either a single PDE or a mixture of PDE activities). The degree of phosphodiesterase inhibition is determined by calculating the amount of radioactivity released in drug-treated reactions and comparing those against a control sample (a reaction mixture lacking the tested compound but with the drug solvent).

B. Cyclic Nucleotide Measurements

Alternatively, the ability of a compound to inhibit cGMP-PDE activity is reflected by an increase in the levels of cGMP in neoplastic cells exposed to the test compound. The amount of PDE activity can be determined by assaying for the amount of cyclic GMP in the extract of treated cells using a radioimmunoassay (RLA). In this procedure, a neoplastic cell line is incubated with a test compound. After about 24 to 48 hours, the cells are solubilized, and cyclic GMP is purified from the cell extracts. The cGMP is acetylated according to published procedures, such as using acetic anhydride in triethylamine, (Steiner, A. L., Parker, C. W., Kipnis, D. M., *J. Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference).

In addition to observing increases in the content of cGMP in neoplastic cells as a result of incubation with certain test compounds, decreases in the content of cAMP have also been observed. It has been observed that a compound which is useful in the practice of this invention (i.e., one that selectively induces apoptosis in neoplastic cells, but not substantially in normal cells) follows a time course consistent with cGMP-specific PDE inhibition. Initially, the result is an increased cGMP content within minutes, and secondarily, there is a decreased cAMP content within 24 hours. The intracellular targets of these drug actions are being studied further, but current data support the concept that the initial rise in cGMP content and the subsequent fall in cAMP content precede apoptosis in neoplastic cells exposed to test compounds useful in this invention. To determine the cyclic AMP content in cell extracts, radioimmunoassay techniques similar to those described above for cGMP are used.

The change in the ratio of the two cyclic nucleotides may be a more accurate tool for evaluating cGMP-specific phosphodiesterase inhibition activity of test compounds, rather than measuring only the absolute value of cGMP, only the level of cGMP hydrolysis, or only cGMP-specific phosphodiesterase inhibition. In neoplastic cells not treated with anti-neoplastic compounds, the ratio of cGMP content/cAMP content is in the 0.03–0.05 range (i.e., 300–500 fmol/mg protein cGMP content over 6000–8000 fmol/mg protein cAMP content). After exposure to desirable anti-neoplastic compounds, that ratio increases several fold (preferably at least about a three-fold increase) as the result of an initial increase in cyclic GMP and the later decrease in cyclic AMP.

Specifically, it has been observed that particularly desirable compounds achieve an initial increase in cGMP content in treated neoplastic cells to a level of cGMP greater than about 500 fmol/mg protein. In addition, particularly desirable compounds cause the later decrease in cAMP content in treated neoplastic cells to a level of cAMP less than about 4000 fmol/mg protein.

Verification of the cyclic nucleotide content may be obtained by determining the turnover or accumulation of cyclic nucleotides in intact cells. To measure the levels of cAMP in intact cells $^3$H-adenine prelabeling is used according to published procedures (Whalin M. E., R. L. Garrett Jr., W. J. Thompson, and S. J. Stada, "Correlation of cell-free brain cyclic nucleotide phosphodiesterase activities to cyclic AMP decay in intact brain slices", *Sec. Mess. and Phos. Protein Research*, 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studies with intact cell prelabeling according to published procedures (Reynolds, P. E., S. J. Strada and W. J. Thompson, "Cyclic GMP accumulation in pulmonary microvascular endothelial cells measured by intact cell prelabeling," *Life Sci.*, 60:909–918, 1997, which is incorporated herein by reference).

C. Tissue Sample Assay

The cGMP-specific PDE inhibitory activity of a test compound can also be determined from a tissue sample. Tissue biopsies from humans or tissues from anesthetized animals are collected from subjects exposed to the test compound. Briefly, a sample of tissue is homogenized and a known amount of the homogenate is removed for protein analysis. From the remaining homogenate, the protein is allowed to precipitate. Next, the homogenate is centrifuged and both the supernatant and the pellet are recovered. The supernatant is assayed for the amount of cyclic nucleotides present using RIA procedures as described above.

D. Experimental Results

1. Introduction

The amount of cGMP-specific inhibition is determined by comparing the activity of the cGMP-specific PDEs in the presence and absence of the test compound. Inhibition of cGMP-PDE activity is indicative that the compound is useful for treating neoplasia in combination with a cisplatin derivative. Significant inhibitory activity, greater than that of the benchmark, exisulind, and preferably greater than 50% at a concentration of 10 $\mu$M or below, is indicative that a compound should be further evaluated for antineoplastic properties. The term "exisulind" means (Z)-5-fluoro-2-methyl-1-[[4-(methylsulfonyl)phenyl]methylene]indene-3-yl acetic acid or a salt thereof. (See, Pamukcu and Brendel, U.S. Pat. No. 5,401,774.)

2. cGMP-PDE Inhibition Assay

Figure 4:
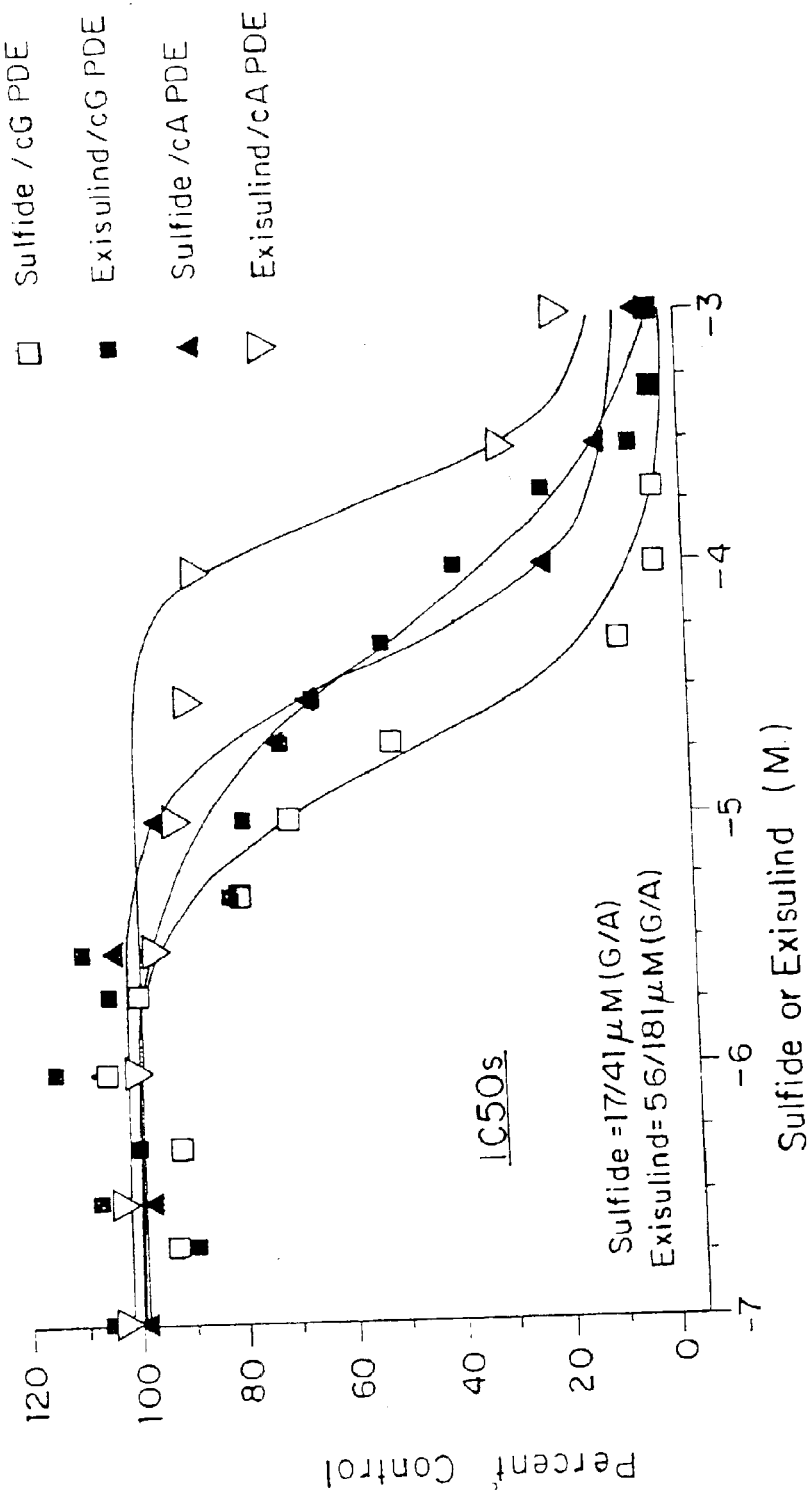
FIG. 4 illustrates the inhibitory effects of sulindac sulfide and exisulind on PDE4 and PDE5 purified from cultured tumor cells.

Reference compounds and test compounds were analyzed for their cGMP-PDE inhibitory activity in accordance with the protocol for the assay described supra. FIG. 4 shows the effect of various concentrations of sulindac sulfide and exisulind on either PDE4 or cGMP-PDE activity purified from human colon HT-29 cultured tumor cells, as described previously (W. J. Thompson et al., supra). The IC$_{50}$ value of sulindac sulfide for inhibition of PDE4 was 41 $\mu$M, and for inhibition of cGMP-PDE was 17 $\mu$M. The IC$_{50}$ value of exisulind for inhibition of PDE4 was 181 $\mu$M, and for inhibition of cGMP-PDE was 56 $\mu$M. These data show that both sulindac sulfide and exisulind inhibit phosphodiesterase activity. Both compounds show selectivity for the cGMP-PDE isoenzyme forms over PDE4 isoforms.

Figure 5A:
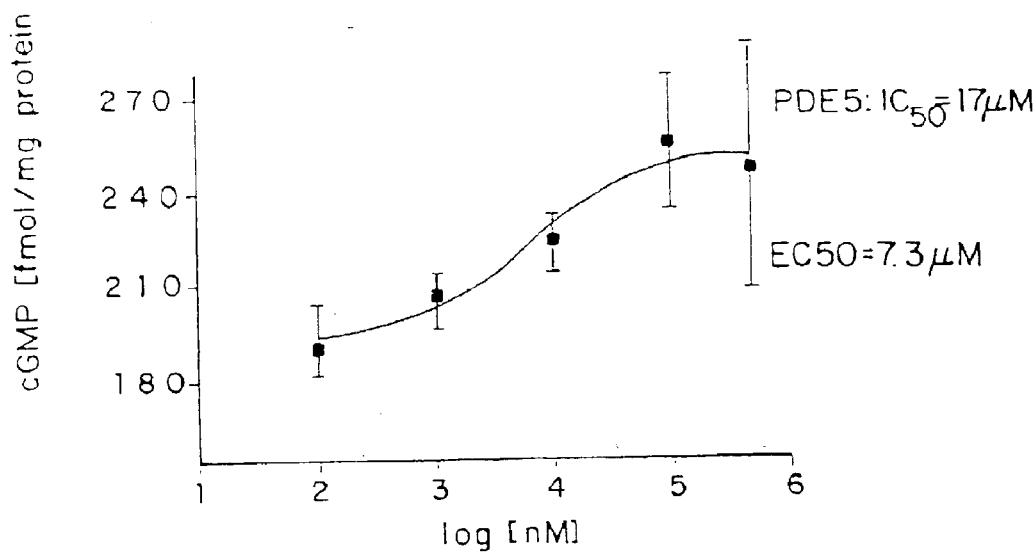
FIGS. 5A and 5B illustrate the effects of sulindac sulfide on cyclic nucleotide levels in HT-29 cells.
Figure 5B:
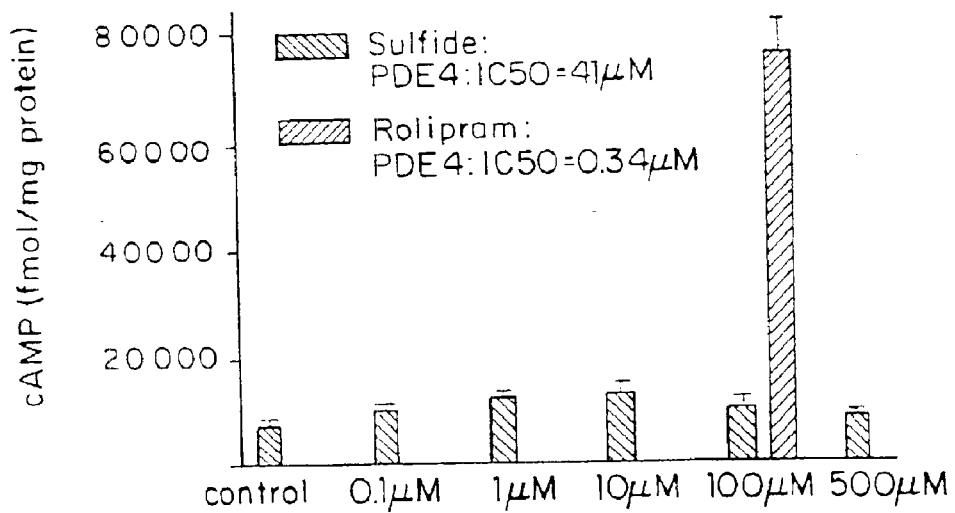

FIG. 5 shows the effects of sulindac sulfide on either cGMP or cAMP production as determined in cultured HT-29 cells in accordance with the assay described, supra. HT-29 cells were treated with sulindac sulfide for 30 minutes and cGMP or cAMP was measured by conventional radioimmunoassay method. As indicated, sulindac sulfide increased the levels of cGMP by greater than 50% with an EC$_{50}$ value of 7.3 $\mu$M (FIG. 5A, top). Levels of cAMP were unaffected by treatment, although a known PDE4 inhibitor, rolipram, increased cAMP levels (FIG. 5B, bottom). The data demonstrate the pharmacological significance of inhibiting cGMP-PDE, relative to PDE4.

Figure 6:
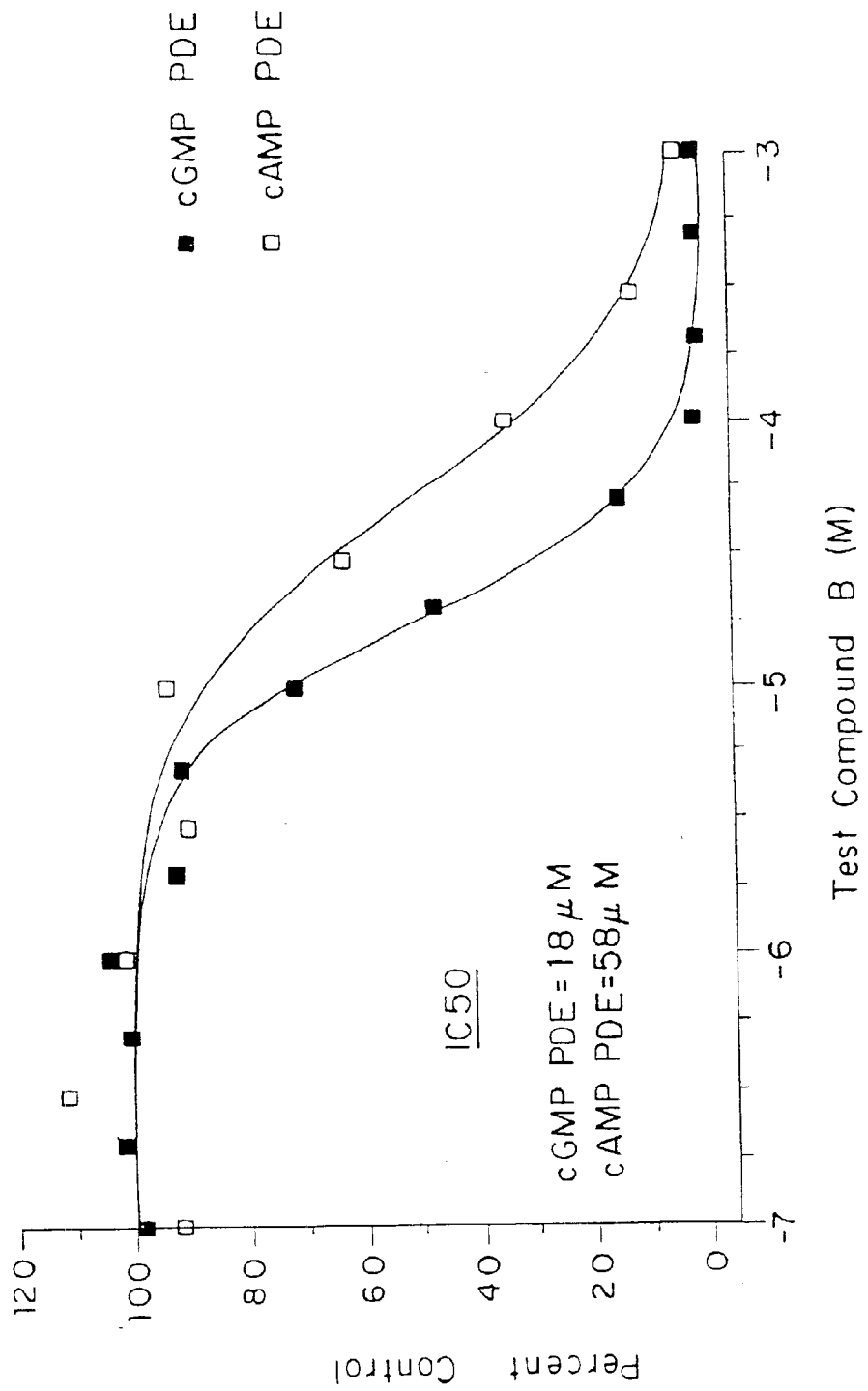
FIG. 6 illustrates the phosphodiesterase inhibitory activity of Compound B.

FIG. 6 shows the effect of the indicated dose of test Compound B, described below, on either cGMP-PDE or PDE4 isozymes of phosphodiesterase. The calculated IC$_{50}$ value was 18 $\mu$M for cGMP-PDE and 58 $\mu$M for PDE4.

Figure 7:
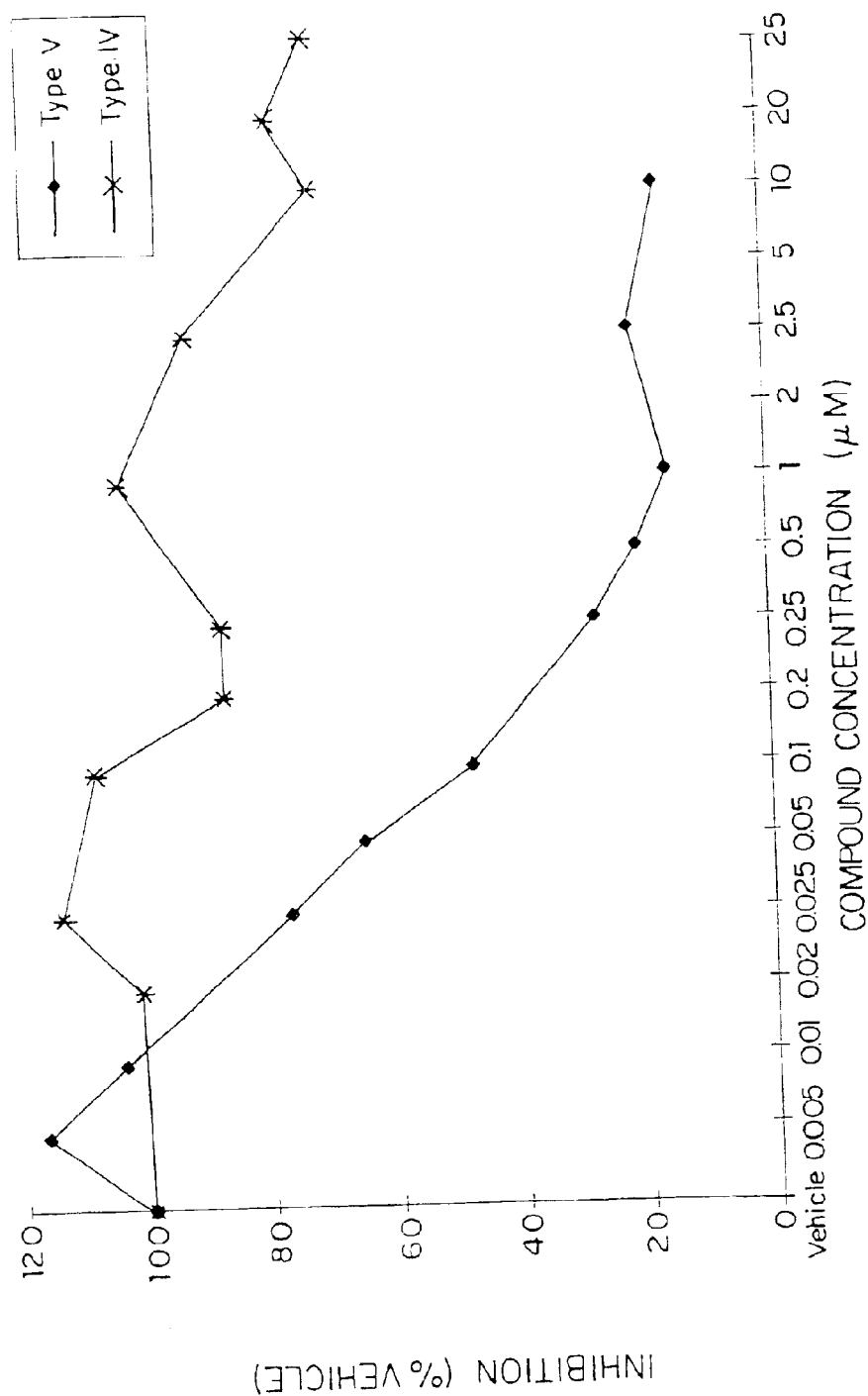
FIG. 7 illustrates the phosphodiesterase inhibitory activity of Compound E.

FIG. 7 shows the effect of the indicated dose of test Compound E, described below, on either PDE4 or cGMP-PDE. The calculated ID$_{50}$ value was 0.08 $\mu$M for cGMP-PDE and greater than 25 $\mu$M for PDE4.

Compounds

A number of compounds were examined in the various protocols and screened for potential use in treating neoplasia. The results of these tests are reported below. The test compounds are hereinafter designated by a letter code that corresponds to the following:

A—rac-threo-(E)-1-(N,N'-diethylaminoethanethio)-1-(butan-1',4'-olido)-[3',4':1,2]-6-fluoro-2-methyl-3-(p-methylsulfonylbenzylidene)-indan;

B—(Z)-5-Fluoro-2-methyl-1-(3,4,5-trimethoxybenzylidene)-3-acetic acid;

C—(Z)-5-Fluoro-2-methyl-1-(p-chlorobenzylidene)-3-acetic acid;

D—rac-(E)-1-(butan-1',4'-olido)-[3'4':1,2]-6-fluoro-2-methyl-3-(p-methylsulfonylbenzlidene)-1S-indanyl-N-acetylcysteine;

E—(Z)-5-Fluoro-2-methyl-1-(3,4,5-trimethoxybenzylidene)-3-indenylacetamide, N-benzyl;

F—(Z)-5-Fluoro-2-methyl-1-(p-methylsulfonylbenzylidene)-3-indenylacetamide, N,N'-dicyclohexyl;

G—ribo-(E)-1-Triazolo-[2',3':1",3"]-1-(butan-1',4'-olido)-[3',4':1,2]-6-fluoro-2-methyl-3-(p-methylsulfonylbenzylidene)-idan: and H—rac-(E)-1-(butan-1',4'-olido)-[3',4':1,2]-6-fluoro-2-methyl-3-(p-methylsulfonylbenzylidene)-1S-indanyl-glutathione).

TABLE 2

| cGMP PDE Inhibitory Activity Among a Series of Compounds | |
|---|---|
| Reference compounds | % Inhibition at 10 $\mu$M |
| Indomethacin | 34 |
| MY5445 | 86 |
| Sulindac sulfide | 97 |
| Exisulind | 39 |
| Test compounds | % Inhibition at 100 $\mu$M |
| A | <25 |
| B | <25 |
| C | <25 |
| D | 36 |
| E | 75 |

The above compounds in Table 2 were evaluated for PDE inhibitory activity in HT-29 cells, as described in the protocol, supra. Of the compounds that did not inhibit COX, only Compound E was found to cause greater than 50% inhibition at 10 $\mu$M. As noted in FIG. 6, Compound B showed inhibition of greater than 50% at a dose of 20 $\mu$M. Therefore, depending on the dosage level used in a single dose test, some compounds may be screened out that otherwise may be active at slightly higher doses. The dosage used is subjective and may be lowered to identify even more potent compounds after active compounds are formed at certain concentration levels.

III. Determining Whether a Compound Reduces the Number of Tumor Cells

In an alternate embodiment, the preferred cGMP-specific inhibitors useful in the practice of this invention are selected by further determining whether the compound reduces the growth of tumor cells in vitro. Various cell lines can be used depending on the tissue to be tested. For example, these cell lines include: SW-480—colonic adenocarcinoma; HT-29—colonic adenocarcinoma: A-427—lung adenocarcinoma; MCF-7—breast adenocarcinoma: UACC-375—melanoma line: and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anticancer drugs.

A. Tumor Inhibition in the HT-29 Cell Line

A compound's ability to inhibit tumor cell growth can be measured using the HT-29 human colon carcinoma cell line obtained from ATCC (Bethesda, Md.). HT-29 cells have previously been characterized as a relevant colon tumor cell culture model (Fogh, J., and Trempe, G. In: *Human Tumor Cells in Vitro*, J. Fogh (ed.), Plenum Press, New York, pp. 115–159, 1975). Briefly, after being grown in culture, HT-29 cells are fixed by the addition of cold trichloroacetic acid. Protein levels are measured using the sulforhodamine B (SRB) colorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," *J. Natl. Cancer Inst.* 82: 1107–1112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Experimental Results

1. Introduction

Significant tumor cell growth inhibition, greater than about 50% at a dose of 100 μM or below is further indicative that the compound is useful for treating neoplastic lesions. Preferably, an $IC_{50}$ value is determined and used for comparative purposes. This value is the concentration of drug needed to inhibit tumor cell growth by 50% relative to the control. Preferably, the $IC_{50}$ value should be less than 100 μM for the compound to be considered useful for treating neoplastic lesions in combination with a cisplatin derivative according to the method of this invention.

2. Growth Inhibition Assay

Figure 8:
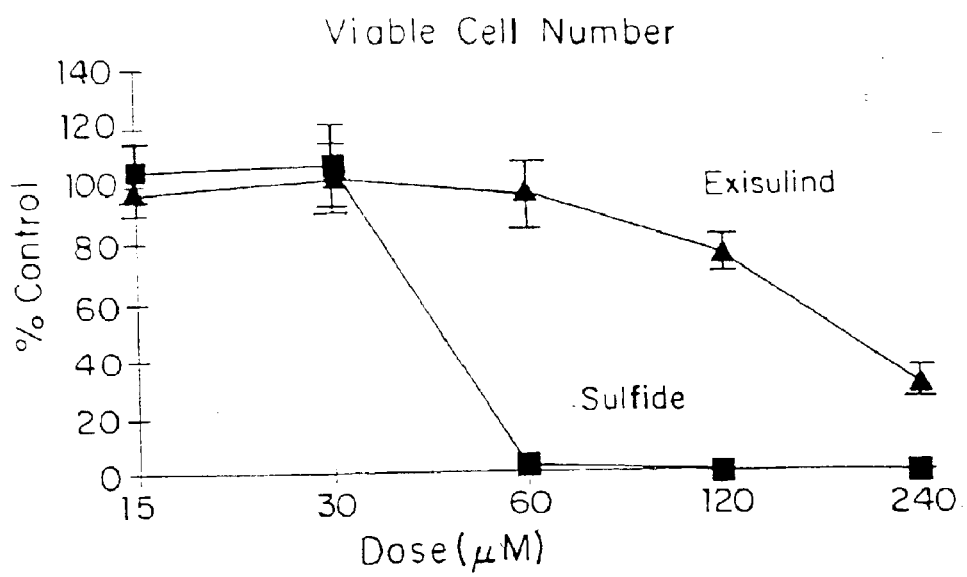
FIG. 8 illustrates the effects of sulindac sulfide and exisulind on tumor cell growth.

Reference compounds and test compounds were analyzed for their cGMP-PDE inhibitory activity in accordance with the protocol for the assay, supra. FIG. 8 shows the inhibitory effect of various concentrations of sulindac sulfide and exisulind on the growth of HT-29 cells. HT-29 cells were treated for six days with various doses of exisulind (triangles) or sulindac sulfide (squares) as indicated. Cell number was measured by a sulforhodamine assay as previously described (Piazza et al., *Cancer Research*, 55: 3110–3116, 1995). The $IC_{50}$ value for sulindac sulfide was approximately 45 μM and for exisulind was approximately 200 μM. The data show that both sulindac sulfide and exisulind are capable of inhibiting tumor cell growth.

Figure 9A:
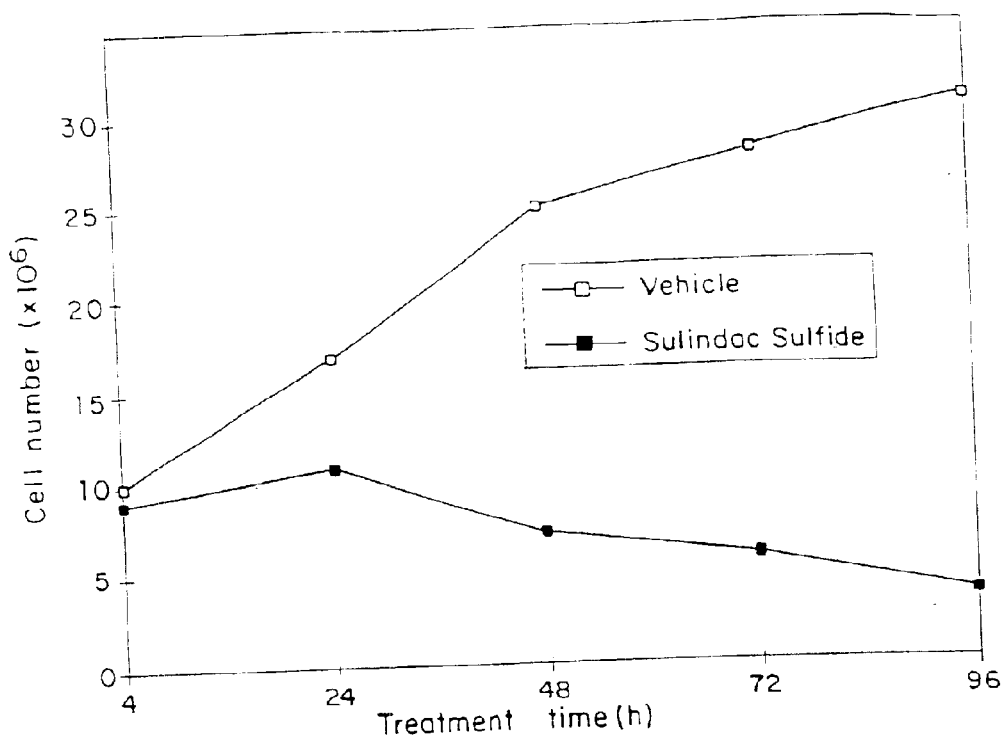
FIGS. 9A and 9B illustrate the growth inhibitory and apoptosis-inducing activity of sulindac sulfide and control (DMSO).
Figure 9B:
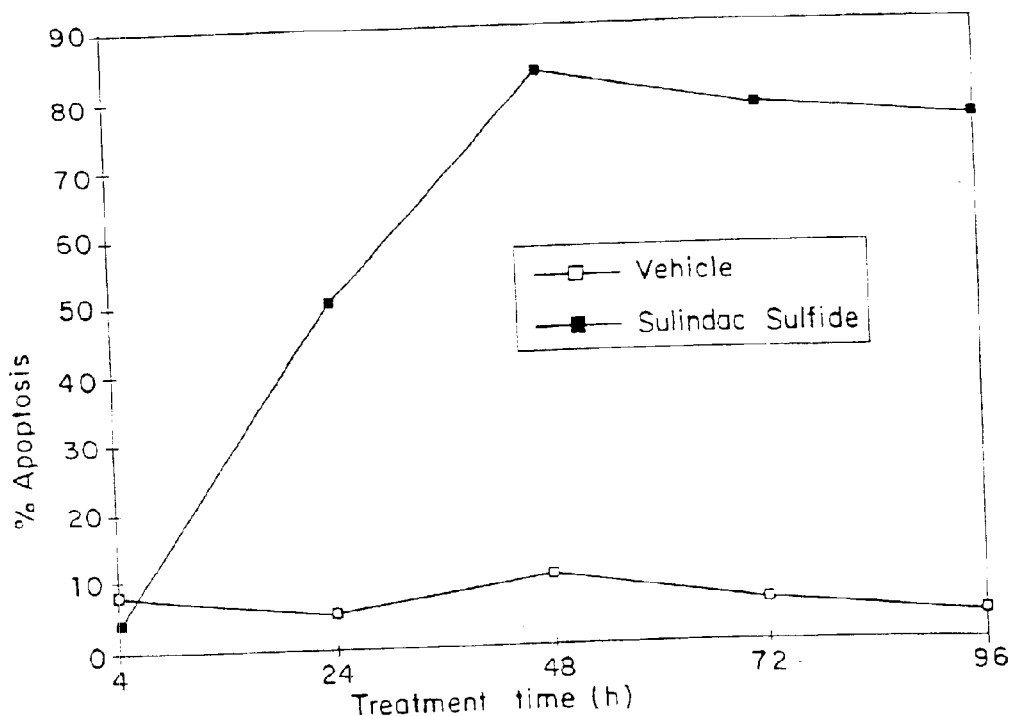

FIG. 9 shows the growth inhibitory and apoptosis-inducing activity of sulindac sulfide. A time course experiment is shown involving HT-29 cells treated with either vehicle, 0.1% DMSO (open symbols) or sulindac sulfide, 120 μM (closed symbols). Growth inhibition (FIG. 9A, top) was measured by counting viable cells after trypan blue staining. Apoptosis (FIG. 9B, bottom) was measured by morphological determination following staining with acridine orange and ethidium bromide as described previously (Duke and Cohen, In: Current Protocols in Immunology, 3 171–3.17.16, New York, John Wiley and Sons, 1992). The data demonstrate that sulindac sulfide is capable of inhibiting tumor cell growth and that the effect is accompanied by an increase in apoptosis. All data were collected from the same experiment.

Figure 10:
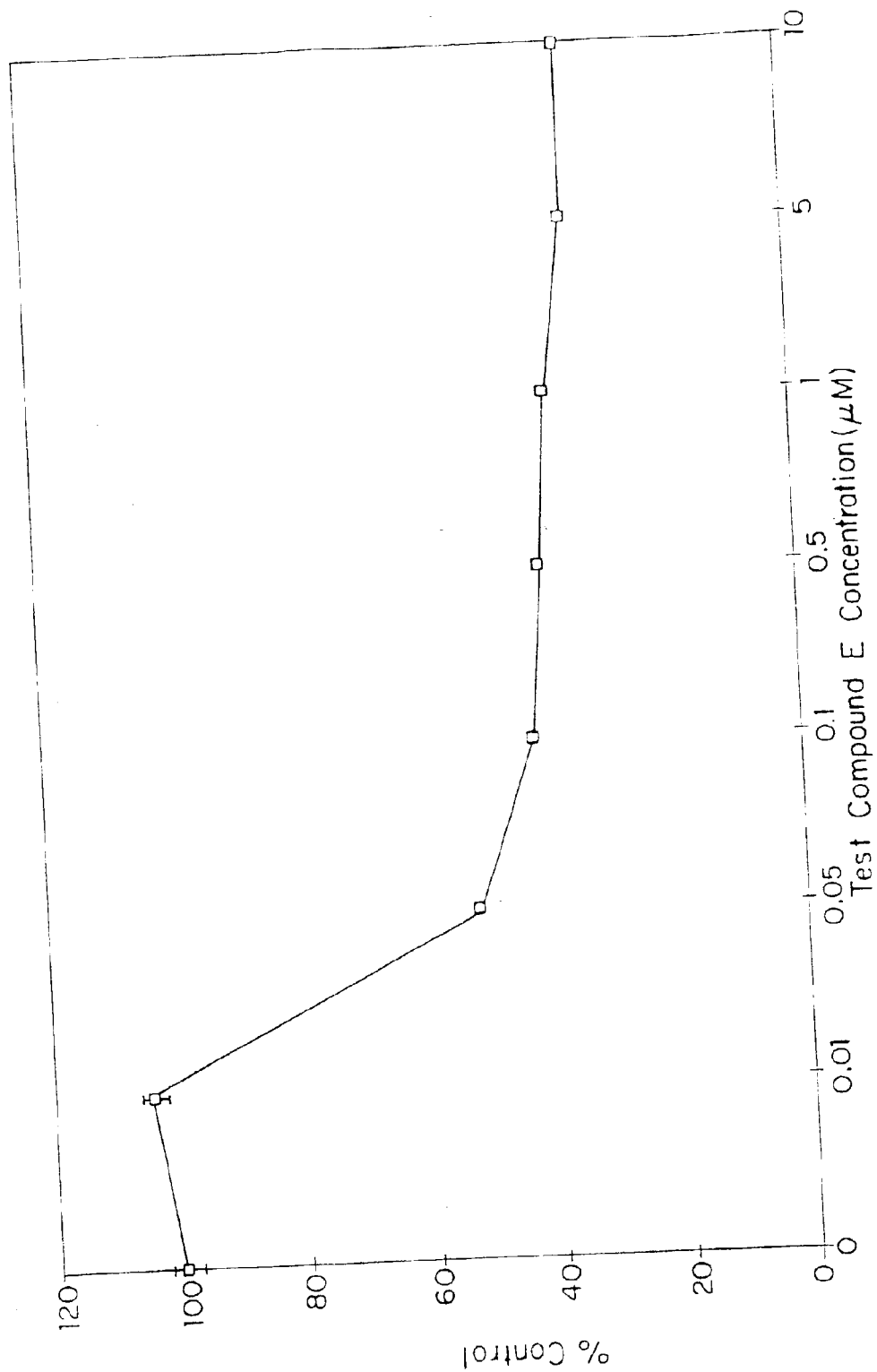
FIG. 10 illustrates the growth inhibitory activity of compound E.

FIG. 10 shows the growth inhibitory activity of test Compound E. HT-29 colon adenocarcinoma cells were treated with the indicated concentration of Compound E for six days and cell number was determined by the SRB assay. The calculated $IC_{50}$ value was 0.04 μM.

TABLE 3

Growth Inhibitory Activity Among a Series of Compounds

| Reference compounds | % Inhibition at 100 μM |
| --- | --- |
| Indomethacin | 75 |
| MY5445 | 88 |
| Sulindac sulfide | 88 |
| Exisulind | <50 |
| E4021 | <50 |
| sildenafil | <50 |
| zaprinast | <50 |

| Test compounds | % Inhibition at 100 μM |
| --- | --- |
| A | 68 |
| B | 77 |
| C | 80 |
| D | 78 |
| E | 62 |

In accordance with the screening protocol, supra, Compounds A through E were tested for growth inhibitory activity, as reported in Table 3 above. All the test compounds showed activity exceeding the benchmark exisulind at a 100 μM single dose test.

The growth inhibitory activity for a series of phosphodiesterase inhibitors was determined. The data are shown in Table 4 below. HT-29 cell were treated for 6 days with various inhibitors of phosphodiesterase. Cell growth was determined by the SRB assay described supra. The data below taken with those above show that inhibitors of the cGMP-specific PDE activity were effective for inhibiting tumor cell growth.

TABLE 4

Growth Inhibitory Data for PDE Inhibitors

| Inhibitor | Reported Selectivity | Growth inhibition ($IC_{50}$ μM) |
| --- | --- | --- |
| 8-methoxy-IBMX | PDE1 | >200 μM |
| Milrinone | PDE3 | >200 μM |
| RO-20-1724 | PDE4 | >200 μM |
| MY5445 | PDE5 | 5 μM |
| IBMX | Non-selective | >100 μM |
| Zaprinast | PDE5 | >100 μM |
| Sildenafil | PDE5 | >100 μM |
| E4021 | PDE5 | >100 μM |

To show the effectiveness of cGMP-specific PDE inhibition on various forms of neoplasia, compounds were tested on numerous cell lines. The effects of sulindac sulfide and exisulind on various cell lines was determined. The data are shown in Table 5 below. The $IC_{50}$ values were determined by the SRB assay. The data show the effectiveness of these compounds on a broad range of neoplasias, with effectiveness at comparable dose range. Therefore, compounds selected for cGMP-specific PDE inhibition in combination with a cisplatin derivative should be useful for treating neoplasia, in particular ovarian and testicular cancers.

TABLE 5

Growth Inhibitory Data of Various Cell Lines

| | $IC_{50}$ ($\mu$M)* | | |
|---|---|---|---|
| Cell Type Tissue specificity | Selindac sulfide | Exisulind | Compound E |
| HT-29, Colon | 60 | 120 | 0.10 |
| HCT116, Colon | 45 | 90 | |
| MCF7S, Breast | 30 | 90 | |
| UACC375, Melanoma | 50 | 100 | |
| A-427, Lung | 90 | 130 | |
| Bronchial Epithelial Cells | 30 | 90 | |
| NRK, kidney (non ras-transformed) | 50 | 180 | |
| KNRK, Kidney (ras transformed) | 60 | 240 | |
| Human Prostate Carcinoma PC3 | | 82 | 0.90 |
| Colo 205 | | | 1.62 |
| DU-145 | | | 0.10 |
| HCT-15 | | | 0.60 |
| MDA-MB-231 | | | 0.08 |
| MDA-MB-435 | | | 0.04 |

*Determined by neutral red assay as described by Schmid et al., in Proc. AACR Vol 39, p. 195 (1998).

IV. Determining Whether a Compound Induces Apoptosis

In a second alternate embodiment, preferably, the cGMP-specific PDE inhibitors useful in combination with a cisplatin derivative in the practice of this invention induce apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blobbing, condensation of cytoplasm, and the activation of endogenous endonucleases.

Apoptosis occurs naturally during normal tissue turnover and during embryonic development of organs and limbs. Apoptosis also is induced by cytotoxic T-lymphocytes and natural killer cells, by ionizing radiation, and by certain chemotherapeutic drugs. Inappropriate regulation of apoptosis is thought to play an important role in many pathological conditions including cancer, AIDS, Alzheimer's disease, etc. Cyclic GMP-specific PDE inhibitors useful in this invention can be selected based on their ability to induce apoptosis in cultured tumor cells maintained under conditions as described above.

Treatment of cells with test compounds involves either pre- or post-confluent cultures and treatment for two to seven days at various concentrations of the compound in question. Apoptotic cells are measured by combining both the attached and "floating" compartments of the cultures. The protocol for treating tumor cell cultures with sulindac and related compounds to obtain a significant amount of apoptosis has been described in the literature. (See, Piazza, G. A., et al., *Cancer Research*, 55:3110–16, 1995, which is incorporated herein by reference). The novel features include collecting both floating and attached cells, identification of the optimal treatment times and dose range for observing apoptosis, and identification of optimal cell culture conditions.

A. Analysis of Apoptosis by Morphological Observation

Following treatment with a test compound, cultures can be assayed for apoptosis and necrosis by fluorescent microscopy following labeling with acridine orange and ethidium bromide. The method for measuring apoptotic cell number has previously been described by Duke & Cohen, "Morphological And Biochemical Assays Of Apoptosis," *Current Protocols In Immunology*, Coligan et al., eds., 3.17.1–3.17.16 (1992, which is incorporated herein by reference).

For example, floating and attached cells can be collected, and aliquots of cells can be centrifuged. The cell pellet can then be resuspended in media and a dye mixture containing acridine orange and ethidium bromide. The mixture can then be examined microscopically for morphological features of apoptosis.

B. Analysis of Apoptosis by DNA Fragmentation

Apoptosis can also be quantified by measuring an increase in DNA fragmentation in cells which have been treated with test compounds. Commercial photometric ELA for the quantitative in vitro determination of cytoplasmic histone-associated-DNA-fragments (mono- and oligonucleosomes) are available (Cell Death Detection ELISA$^{okys}$, Cat. No. 1.774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by washing, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

Fold stimulation (FS=$OD_{max}OD_{ven}$), an indicator of apoptotic response, is determined for each compound tested at a given concentration. $EC_{50}$ values may also be determined by evaluating a series of concentrations of the test compound.

C. Experimental Results

1. Introduction

Statistically significant increases of apoptosis (i.e., greater than 2 fold stimulation at a concentration of 100 $\mu$M) are further indicative that the cGMP-specific PDE inhibitor is useful in combination with a cisplatin derivative in the practice of this invention. Preferably, the $EC_{50}$ value for apoptotic activity should be less than 100 $\mu$M for the compound to be further considered for potential use for treating neoplastic lesions. $EC_{50}$ is herein defined as the concentration that causes 50% induction of apoptosis relative to vehicle treatment.

2. Apoptosis Assay

Figure 11A:
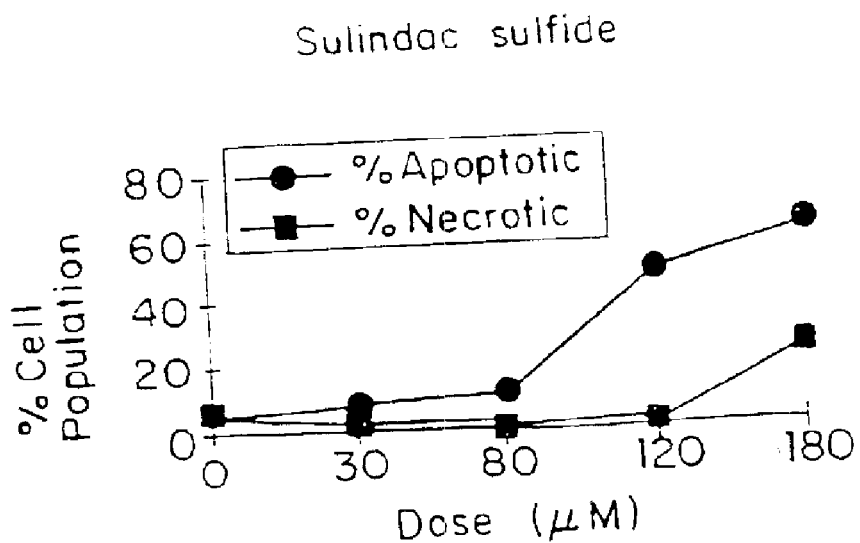
FIGS. 11A and 11B illustrate the effects of sulindac sulfide and exisulind on apoptosis and necrosis of HT-29 cells.
Figure 11B:
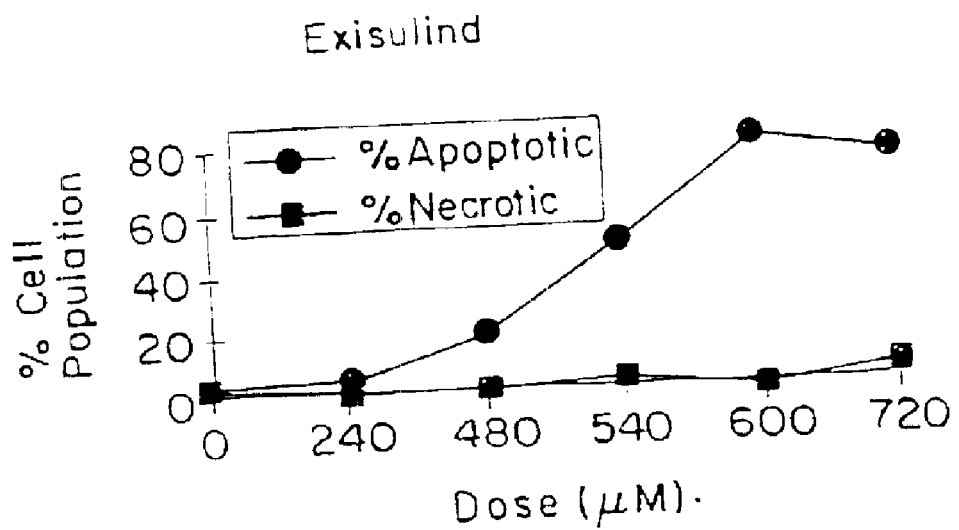

Reference compounds and test compounds were analyzed for their cGMP-specific PDE inhibitory activity in accordance with the protocols for the assay, supra. In accordance with those protocols, FIG. 11 shows the effects of sulindac sulfide and exisulind on apoptotic and necrotic cell death. HT-29 cells were treated for six days with the indicated dose of either sulindac sulfide or exisulind. Apoptotic and necrotic cell death was determined as previously described (Duke and Cohen, In: Current Protocols in Immunology, 3.17.1–3.17.16, New York, John Wiley and Sons, 1992). The data show that both sulindac sulfide and exisulind are capable of causing apoptotic cell death without inducing necrosis. All data were collected from the same experiment.

Figure 12A:
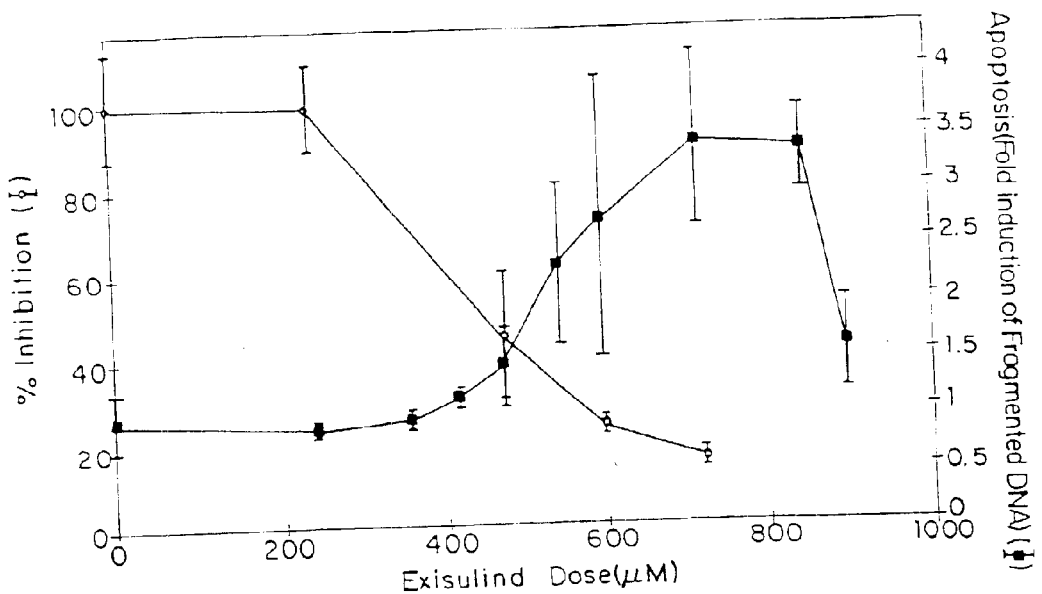
FIGS. 12A and 12B illustrate the effects of sulindac sulfide and exisulind on HT-29 cell growth inhibition and apoptosis induction as determined by DNA fragmentation.
Figure 12B:
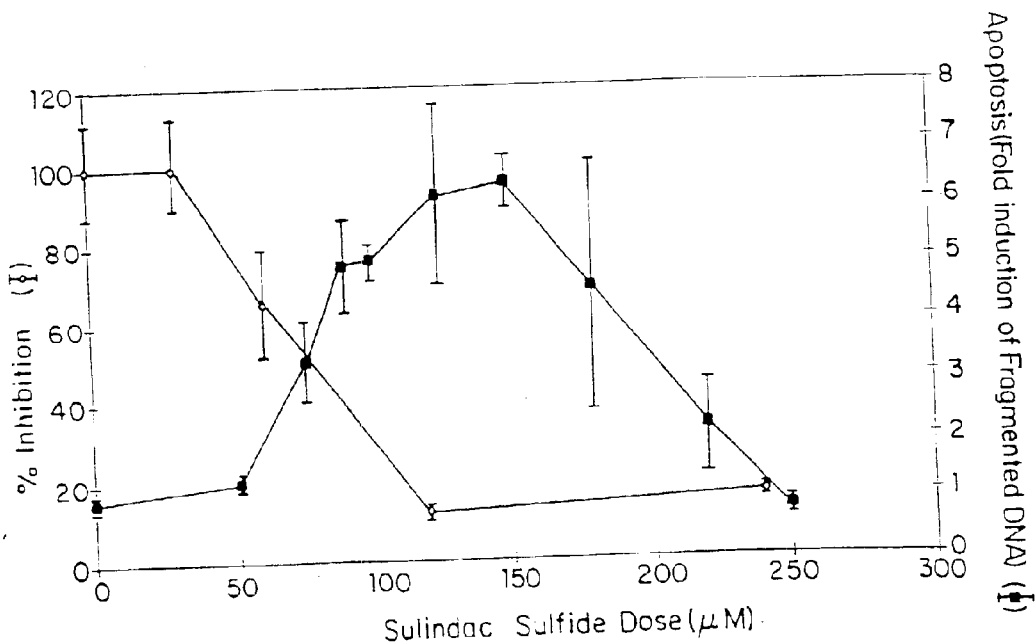

FIG. 12 shows the effect of sulindac sulfide and exisulind on tumor growth inhibition and apoptosis induction as determined by DNA fragmentation. The top FIG. (12A) shows growth inhibition (open symbols, left axis) and DNA fragmentation (closed symbols, right axis) by exisulind. The bottom FIG. (12B) shows growth inhibition (open symbols) and DNA fragmentation (closed symbols) by sulindac sulfide. Growth inhibition was determined by the SRB assay after six days of treatment. DNA fragmentation was determined after 48 hours of treatment. All data was collected from the same experiment.

Figure 13:
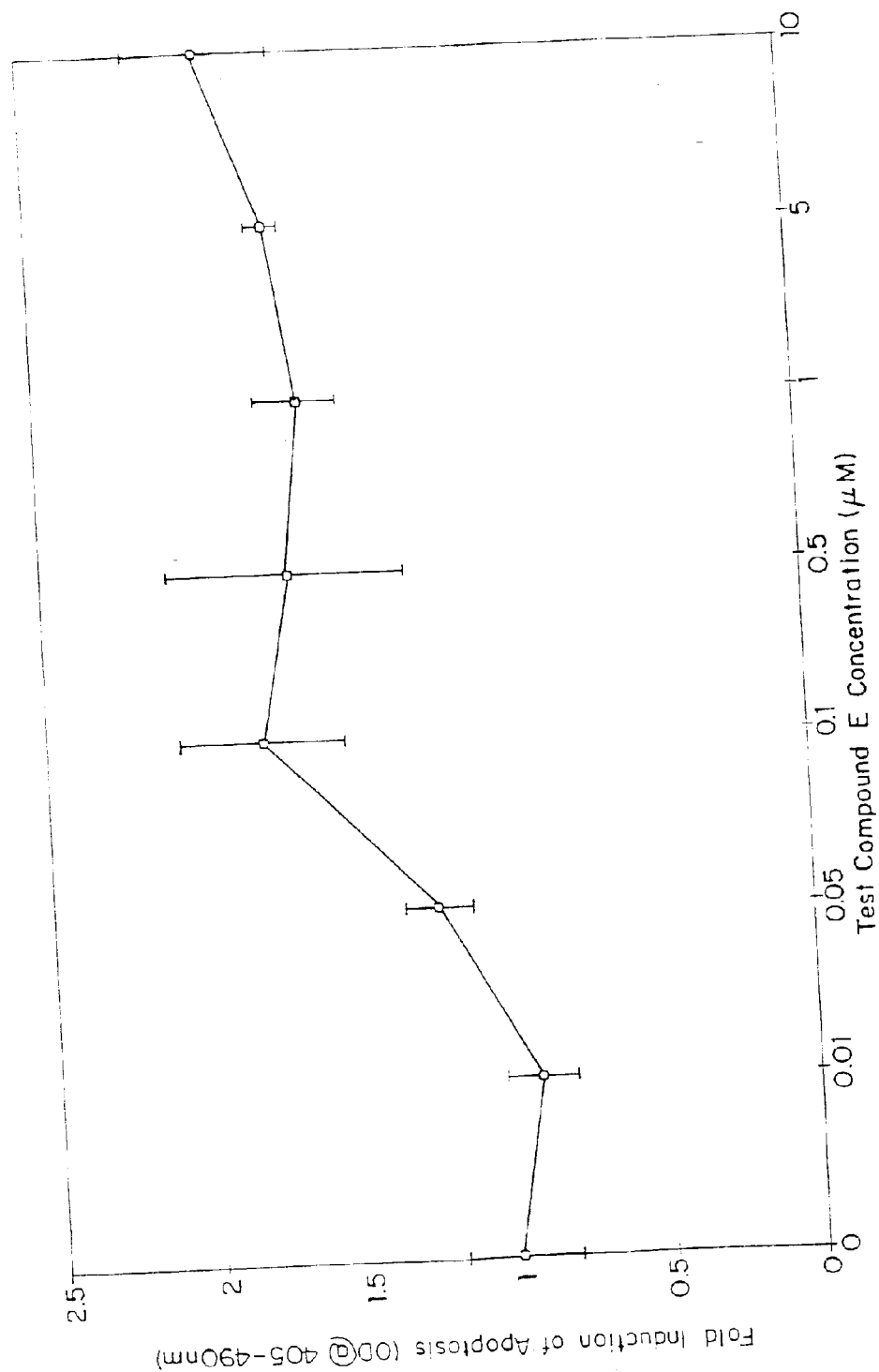
FIG. 13 illustrates the apoptosis inducing properties of Compound E.

FIG. 13 shows the apoptosis inducing properties of Compound E. HT-29 colon adenocarcinoma cells were treated with the indicated concentration of Compound E for 48 hours and apoptosis was determined by the DNA fragmentation assay. The calculated $EC_{50}$ value was 0.05 $\mu M$.

Figure 14:
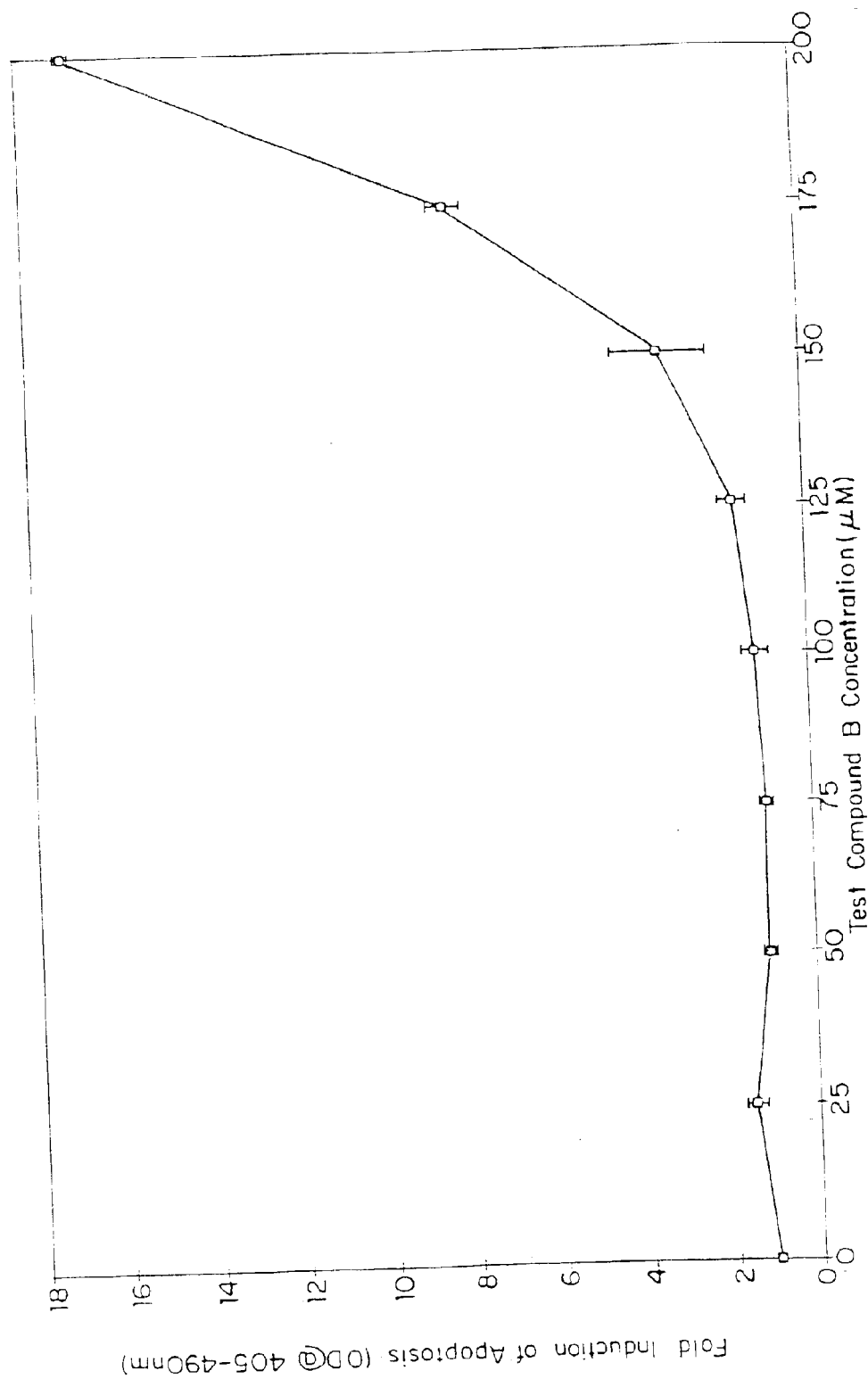
FIG. 14 illustrates the apoptosis inducing properties of Compound B.

FIG. 14 shows the apoptosis inducing properties of Compound B. HT-29 colon adenocarcinoma cells were treated with the indicated concentration of Compound B for 48 hours and apoptosis was determined by the DNA fragmentation assay. The calculated $EC_{50}$ value was approximately 175 $\mu M$.

TABLE 6

Apoptosis Inducing Activity Among a Series of Compounds

| Reference compounds | Fold Induction at 100 $\mu M$ |
|---|---|
| Indomethacin | <2.0 |
| MY5445 | 4.7 |
| Sulindac sulfide | 7.9 |
| Exisulind | <2.0 |
| E4021 | <2.0 |
| Zaprinast | <2.0 |
| Sildenafil | <2.0 |
| EHNA | <2.0 |

| Test compounds | Fold induction at 100 $\mu M$ |
|---|---|
| A | <2.0 |
| B | 3.4 |
| C | 5.6 |
| D | <2.0 |
| E | 4.6 |

In accordance with the fold induction protocol, supra, Compounds A through E were tested for apoptosis inducing activity, as reported in Table 6 above. Compound B, C, and E showed significant apoptotic inducing activity, greater than 2.0 fold, at a dosage of 100 $\mu M$. Of these three compounds, at this dosage, only Compounds B and E did not inhibit COX but did inhibit cGMP-specific PDE.

The apoptosis inducing activity for a series of phosphodiesterase inhibitors was determined. The data are shown in Table 7 below. HT-29 cell were treated for 6 days with various inhibitors of phosphodiesterase. Apoptosis and necrosis were determined morphologically after acridine orange and ethidium bromide labeling in accordance with the assay described, supra. The data show cGMP-specific PDE inhibition represents a unique pathway to induce apoptosis in neoplastic cells.

TABLE 7

Apoptosis Induction Data for PDE Inhibitors

| Inhibitor | Reported Selectivity | % Apoptosis | % Necrosis |
|---|---|---|---|
| Vehicle | | 8 | 6 |
| 8-methoxy-IBMX | PDE1 | 2 | 1 |
| Milrinone | PDE3 | 18 | 0 |
| RO-20-1724 | PDE4 | 11 | 2 |
| MY5445 | PDE5 | 80 | 5 |
| IBMX | Non-selective | 4 | 13 |

V. Mammary Gland Organ Culture Model Tests

A. Introduction

Test compounds identified by the above methods can be tested for antineoplastic activity by their ability to inhibit the incidence of preneoplastic lesions in a mammary gland organ culture system. This mouse mammary gland organ culture technique has been successfully used by other investigators to study the effects of known antineoplastic agents such as NSAIDs, retinoids, tamoxifen, selenium, and certain natural products, and is useful for validation of the methods used to select cGMP-specific PDE inhibitors useful in the present invention.

For example, female BALB/c mice can be treated with a combination of estradiol and progesterone daily, in order to prime the glands to be responsive to hormones in vitro. The animals are sacrificed and thoracic mammary glands are excised aseptically and incubated for ten days in growth media supplemented with insulin, prolactin, hydrocortisone, and aldosterone DMBA (7,12-dimethylbenz(a)anthracene) is added to medium to induce the formation of premalignant lesions. Fully developed glands are then deprived of prolactin, hydrocortisone, and aldosterone, resulting in the regression of the glands but not the premalignant lesions.

The test compound is dissolved in DMSO and added to the culture media for the duration of the culture period. At the end of the culture period, the glands are fixed in 10% formalin, stained with alum carmine, and mounted on glass slides. The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

The incidence of forming mammary lesions is the ratio of the glands with mammary lesions to glands without lesions. The incidence of mammary lesions in test compound treated glands is compared with that of the untreated glands.

B. Activity in Mammary Gland Organ Culture Model

Figure 15:
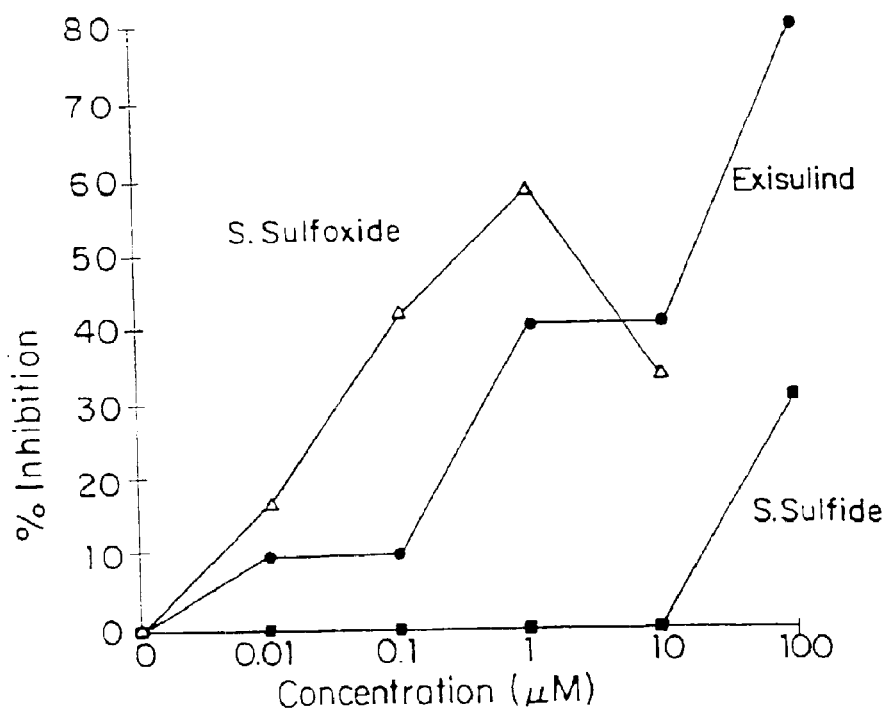
FIG. 15 illustrates the inhibition of pre-malignant, neoplastic lesions in mouse mammary gland organ culture by sulindac metabolites.

FIG. 15 shows the inhibition of premalignant lesions in mammary gland organ culture by sulindac metabolites. Mammary gland organ culture experiments were performed as previously described (Mehta and Moon. *Cancer Research*, 46: 5832–5835, 1986). The results demonstrate that sulindac sulfoxide and exisulind effectively inhibit the formation of premalignant lesions, while sulindac sulfide was inactive. The data support the hypothesis that cyclooxygenase inhibition is not necessary for the anti-neoplastic properties of desired compounds.

Conclusions Regarding Preferred PDE Inhibitors

To identify cGMP-inhibiting compounds that are useful for treating neoplasia in combination with a cisplatin derivative candidate cGMP-inhibiting compounds can be selected by testing them as described above.

Qualitative data of various test compounds and the several protocols are shown in Table 8 below. The data show that exisulind, sulindac sulfide. MY5445, Compound B, and Compound E exhibit the appropriate activity to be used with a cisplatin derivative in the practice of this invention. In addition, those same compounds (except for sulindac sulfide and MY5445) are desirable because they lack COX inhibition activity. The activity of these compounds in the mammary gland organ culture validates the effectiveness of these compounds.

TABLE 8

Activity Profile of Various Compounds

| Compound | COX Inhibition | PDE Inhibition | Growth Inhibition | Apoptosis | Mammary Gland Organ Culture |
|---|---|---|---|---|---|
| Exisulind | − | ++ | −− | ++ | +++ |
| Sulindac sulfide | ++++ | +++ | +++ | +++ | − |
| MY5445 | +++ | +++ | +++ | +++ | + |
| A | − | − | +++ | ++ | ++ |
| B | − | +++ | +++ | +++ | ++ |
| D | − | − | ++ | − | − |
| E | − | ++++ | ++++ | ++++ | ++++ |
| F | − | − | ++ | + | − |
| G | − | − | +++ | ++ | +++ |
| H | − | − | ++ | − | − |

Table 8. Code: Activity of compounds based on evaluating a series of experiments involving tests for maximal activity and potency.
−Not active
÷Slightly active
÷÷Moderately active
÷÷−Strongly active
÷÷−−Highly active Combination Treatment with a Cisplatin Derivative and a PDE Inhibitor The method of this invention involves treating a patient with neoplasia with both an antineoplastic platinum coordination complex and a cGMP-specific PDE inhibitor. There are a number of antineoplastic platinum coordination complexes or cisplatin derivatives. In this regard, the two terms are used interchangeably herein. Various antineoplastic platinum coordination complexes (e.g., cisplatin and carboplasm) are disclosed. Other antineoplastic platinum coordination complexes are disclosed in U.S. Pat. Nos. 4,996,337, 4,946,954, 5,091,521, 5,434,256, 5,527,905, 5,633,243, all of which are incorporated herein by reference. Such compositions collectively disclose non-limiting examples of "antineoplastic platinum coordination complexes" as that term is used herein.

This invention involves using combination therapy to treat a patient with neoplasia. By treating a patient with this combination of pharmaceuticals, a cisplatin derivative and a cGMP-specific PDE inhibitor, therapeutic results can be achieved that are not seen with either drug alone. As explained above, exisulind is one example of an appropriate cGMP-specific PDE inhibitor to be used in combination with a cisplatin derivative in the practice of this invention. Exisulind inhibits both PDE5 and the new cGMP-PDE, and treatment of neoplastic cells with exisulind results in growth inhibition and apoptosis. (See Table 8).

Exisulind and the antineoplastic platinum coordination complex, carboplatin, were tested together to determine their combined effect on the growth of a tumor cell line. The ability of the combination to inhibit tumor cell growth was tested by growing HT-29 cells in exisulind (FGN-1) doses from 25 $\mu$M–400 $\mu$M in the presence of carboplatin doses varying from 1 $\mu$M to 100 $\mu$M. (See FIGS. 15–20) A standard SRB assay (see section III.A.) was performed to determine the drugs' effect on cell growth.

Figure 16:
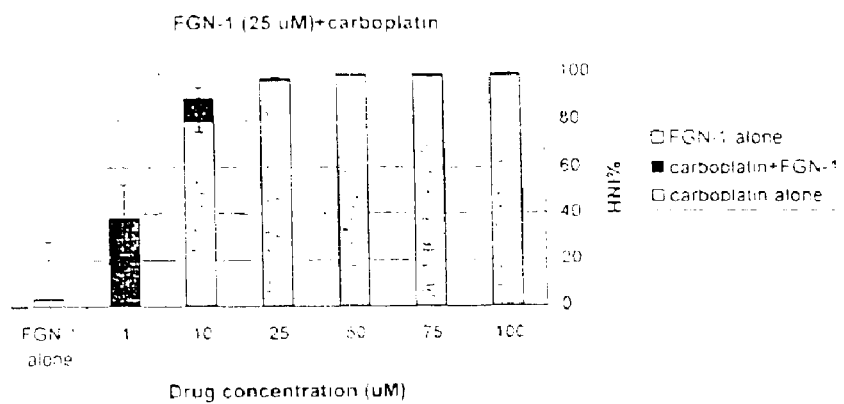
FIG. 16 illustrates the effects of carboplatin and exisulind (FGN-1) on tumor cell growth at 25 $\mu$M exisulind.
Figure 17:
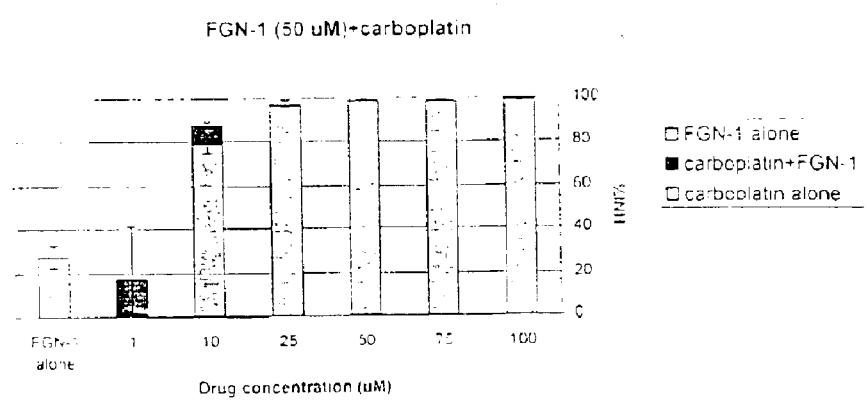
FIG. 17 illustrates the effects of carboplatin and exisulind (FGN-1) on tumor cell growth at 50 $\mu$M exisulind.
Figure 18:
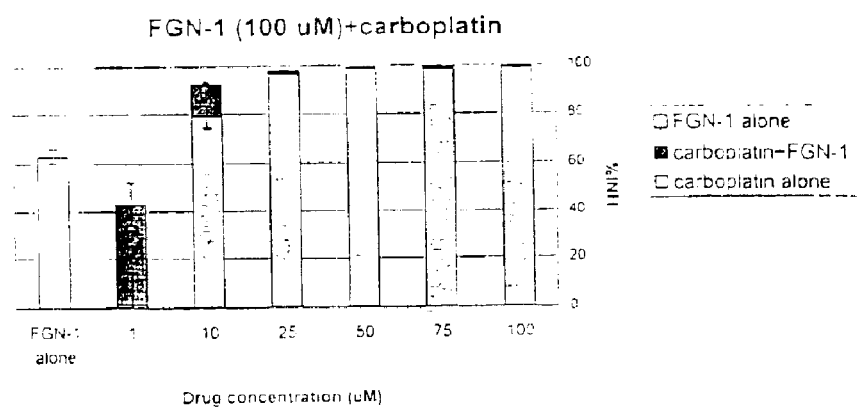
FIG. 18 illustrates the effects of carboplatin and exisulind (FGN-1) on tumor cell growth at 100 $\mu$M exisulind.
Figure 19:
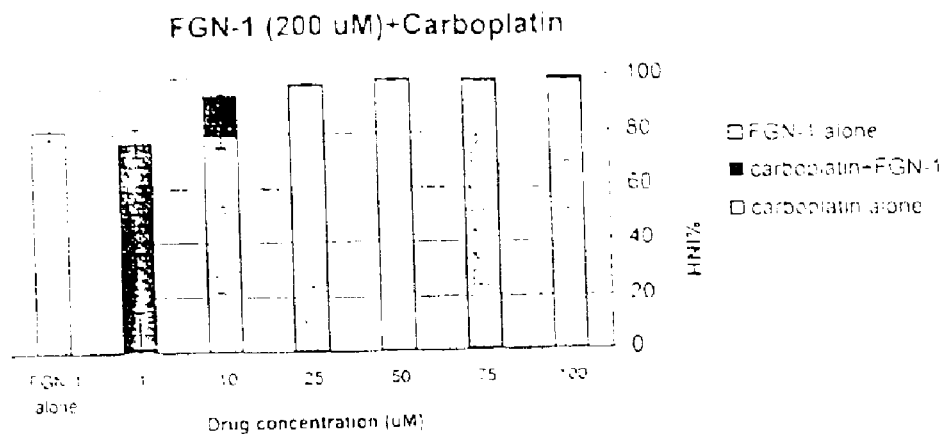
FIG. 19 illustrates the effects of carboplatin and exisulind (FGN-1) on tumor cell growth at 200 $\mu$M exisulind.
Figure 20:
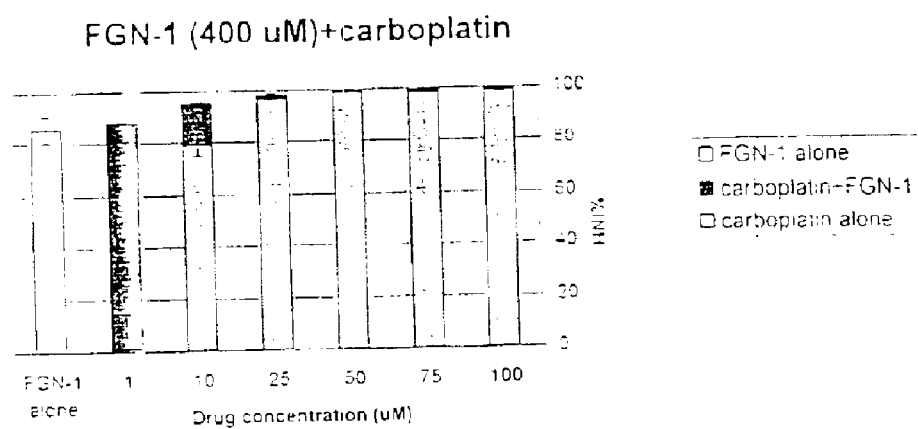
FIG. 20 illustrates the effects of carboplatin and exisulind (FGN-1) on tumor cell growth at 400 $\mu$M exisulind.

The data show the results on inhibition of cell growth after treatment with both exisulind and carboplatin. FIG. 16, for example, illustrates the effects on HT-29 cell grown in 25 $\mu$M exisulind and various doses of carboplatin. The percentage of growth inhibition with FGN-1 (exisulind) alone is shown in the first unshaded bar to the left, labeled FGN-1 alone. The effect on cells grown in 25 $\mu$M FGN-1 combined with 1 $\mu$M taxol is shown in the next bar to the right, labeled 1. As illustrated in FIG. 16, the growth inhibition effects of combining carboplatin with a cGMP-specific PDE inhibitor, such as exisulind, are greater than the effects of either treatment alone. This combined benefit is most pronounced at exisulind doses of 25 $\mu$M to 100 $\mu$M (FIGS. 16–18) and at carboplatin concentrations of 10 $\mu$M or less.

The method of this invention involves using combination therapy to treat patients with neoplasia. Such combination therapy enhances the benefit to the patient without increasing harmful side effects. For example, exisulind is one cGMP-specific PDE inhibitor that can be used in combination with a cisplatin derivative in this invention.

Exisulind has no significant side effects when administered at its recommended dose of 300–400 mg/day. When administered at doses higher than the recommended therapeutic levels, treatment with exisulind can lead to elevated levels of liver enzymes. This effect is reversible, and liver enzymes return to normal levels when the administered dose of exisulind returns to the traditionally recommended level or when treatment is discontinued. The most serious side effects of cisplatin derivatives, on the other hand, are renal insufficiency and myelosuppression. Since the side effects of the two drugs do not overlap, a PDE inhibitor, such as exisulind, can be used in combination with a cisplatin derivative without increasing the harmful side effects of the cisplatin derivative.

A cGMP-specific PDE inhibitor and a cisplatin derivative can be used in combination in at least two different ways. In the first method, the traditionally recommended dose range of the cisplatin derivative is reduced while its beneficial therapeutic effects are maintained and its side effects are attenuated. The second method uses the traditionally recommended dose range of the cisplatin derivative with enhanced activity but without increasing its side effects. In each of these methods, the patient is receiving both drugs, a PDE inhibitor and a cisplatin derivative, either simultaneously or in succession.

The recommended dosage of a cisplatin derivative varies depending on the type of cancer being treated and whether the cisplatin derivative is being used in combination with another chemotherapeutic agent. In the practice of this invention, a cGMP-specific PDE inhibitor is used as an additional element of cancer treatment with a cisplatin derivative alone or with a group of chemotherapeutic agents.

For the treatment of metastatic ovarian tumors, the typical cisplatin dosage is 75 to 100 mg/m$^2$ once every four weeks when used in combination cyclophosphamide (Cytotoxan). Other chemotherapeutics used in combination with cisplatin for ovarian tumors include paclitaxel, cyclophosphamide, or doxorubicin. As a single agent for the treatment of metastatic ovarian tumors, cisplatin is typically administered at a dose of 100 mg/m² once every four weeks.

For advanced bladder cancer, the recommended dose is 50 to 70 mg/m² once every three to four weeks with cisplatin administered as a single agent.

For the treatment of metastatic testicular tumors, the recommended cisplatin dose is 20 mg/m² daily for five days when used in combination with another agent.

The typical dose of carboplatin, used for the treatment of ovarian cancer is 360 mg/m² administered once every 28 days.

In the practice of this invention, for each of the treatment methods mentioned above as well as other possible combinations, treatment with an appropriate cGMP-specific PDE inhibitor is added as an additional element of the therapy. A cGMP-specific PDE inhibitor and an antineoplastic platinum coordination complex are used in combination such that the blood levels of the inhibitor are at approximately the $IC_{50}$ value of the inhibitor for growth inhibition. In the case of exisulind, it is recommended that the dose be about 200 to 400 mg/day administered between two to four times a day.

In one embodiment of this invention, the lower dose methodology, cisplatin is administered at a dosage lower than the traditionally recommended dose of 20, 50, or 75 mg/m² (for the indications above) in each case, in combination with a cGMP-specific PDE inhibitor. Similarly, for carboplatin, a dosage less than 360 mg m² in combination with a cGMP-specific PDE inhibitor is practiced consistent with the lower dose methodology of this invention. Accordingly, the combination of therapies allows the benefits of antineoplastic platinum coordination complex treatment to be maintained while its side effects are reduced.

In the second embodiment, the dosage of cisplatin is maintained at its traditionally recommended dose (e.g., at abut 20 mg m² daily, or between 50 to 70 mg/m² once every three to four weeks, or 75 to 100 mg m² once every four weeks, depending on the type of cancer being treated), and is administered in combination with a cGMP-specific PDE inhibitor. Similarly, for carboplatin, the current recommended dose (about 360 mg/m² administered once every 28 days) can be maintained in combination with a cGMP-specific PDE inhibitor. The combination, in this case, increases the efficacy of antineoplastic platinum coordination complex treatment without increasing its harmful side effects.

In each of the aforementioned methodologies, the antineoplastic platinum coordination complex and the cGMP-specific PDE inhibitor may be administered simultaneously or in succession, one after the other.

Obviously, numerous modifications and variations of the present invention are possible in light of the above teachings. It is therefore to be understood that within the scope of the appended claims, the invention may be practiced otherwise than as specifically described herein.

We claim:

1. A method of treating a patient with neoplastic cells comprising exposing said neoplastic cells to an effective amount of a compound that inhibits PDE5 and cGMP-PDE to cause cyclic GMP to increase in the neoplastic cells and exposing said neoplastic cells to a cisplatin derivative.

2. The method of claim 1 wherein the neoplastic cells are exposed to the cisplatin derivative at the same time cyclic GMP is increased.

3. The method of claim 1 wherein the neoplastic cells are exposed to the cisplatin derivative before or after cyclic GMP is increased.

* * * * *